(12) United States Patent
McInnes et al.

(10) Patent No.: US 9,982,015 B2
(45) Date of Patent: May 29, 2018

(54) CYCLIN BASED INHIBITORS OF CDK2 AND CDK4

(71) Applicant: University of South Carolina, Columbia, SC (US)

(72) Inventors: Campbell McInnes, Irmo, SC (US); Padmavathy Nandha Premnath, Columbia, SC (US); Joshua K. Bolger, Florence, SC (US)

(73) Assignee: University of South Carolina, Columbia, SC (US)

( * ) Notice: Subject to any disclaimer, the term of this patent is extended or adjusted under 35 U.S.C. 154(b) by 0 days. days.

(21) Appl. No.: 15/192,247

(22) Filed: Jun. 24, 2016

(65) Prior Publication Data
US 2017/0218018 A1 Aug. 3, 2017

Related U.S. Application Data

(60) Continuation of application No. 14/492,753, filed on Sep. 22, 2014, now Pat. No. 9,376,465, which is a division of application No. 13/940,407, filed on Jul. 12, 2013, now abandoned, which is a continuation-in-part of application No. 13/851,661, filed on Mar. 27, 2013, now abandoned.

(60) Provisional application No. 61/616,154, filed on Mar. 27, 2012.

(51) Int. Cl.
A61K 38/06 (2006.01)
C07K 7/06 (2006.01)
C07K 5/117 (2006.01)
A61K 38/00 (2006.01)

(52) U.S. Cl.
CPC ............... *C07K 7/06* (2013.01); *A61K 38/06* (2013.01); *C07K 5/1024* (2013.01); *A61K 38/00* (2013.01)

(58) Field of Classification Search
None
See application file for complete search history.

(56) References Cited

U.S. PATENT DOCUMENTS

| | | |
|---|---|---|
| 7,449,544 B2 | 11/2008 | Zheleva et al. |
| 8,566,072 B2 | 10/2013 | McInnes et al. |
| 2006/0281687 A1 | 12/2006 | Andrews et al. |

FOREIGN PATENT DOCUMENTS

WO  WO 2005/042565  5/2005

OTHER PUBLICATIONS

Andrews, et al.; "Design, synthesis, biological activity and structural analysis of cyclic peptide inhibitors targeting the substrate recruitment site of cyclin-dependent kinase complexes," *Organic & Biomolecular Chemistry*, 2004, 2:2735-2341.

Andrews, et al.; "REPLACE: a strategy for iterative design of cyclin-binding groove inhibitors," *Chembiochem*, 2006, 7:1909-1915.

Ball et al.; "Cell-cycle arrest and inhibition of Cdk4 activity by small peptides based on the carboxy-terminal domain of p21WAF1," *Current Biology* 1996, 7:71-80.

Baughn et al.; "A novel orally active small molecule potently induces G1 arrest in primary myeloma cells and prevents tumor growth by specific inhibition of cyclin-dependent kinase 4/6," *Cancer Res* 2006, 66:7661-7667.

Blain; "Switching cyclin D-Cdk4 kinase activity on and off," *Cell Cyle* 2008, 7:892-898.

Brown, et al.; "The structural basis for specificity of substrate and recruitment peptides for cyclin-dependent kinases," *Nature Cell Biology* 1999, 1:438-443.

Chen et al.; "Selective killing of transformed cells by cyclin/cyclin-dependent kinase 2 antagonists," *Proc Natl Acad Sci U S A* 1999, 96:4325-4329.

Kontopidis, et al.; "Truncation and optimisation of peptide inhibitors of cyclin-dependent kinase 2-cyclin a through structure-guided design," *ChemMedChem* 2009, 4:1120-1128.

Day, et al.; "Crystal structure of human CDK4 in complex with a D-type cyclin," *Proc Natl Acad Sci U S A* 2009, 106:4166-4170.

Fischer, et al.; "Recent progress in the discovery and development of cyclin-dependent kinase inhibitors," *Expert Opin Investig Drugs* 2005, 14:457-477.

Fry, et al.; "Specific inhibition of cyclin-dependent kinase 4/6 by PD 0332991 and associated antitumor activity in human tumor xenografts," *Molecular Cancer Therapeutics* 2004, 3:1427-1438.

James, et al.; "Differential modification of p27Kip1 controls its cyclin D-cdk4 inhibitory activity," *Mol Cell Biol* 2008, 28:498-510.

Kontopidis, et al. "Insights into cyclin groove recognition: complex crystal structures and inhibitor design through ligand exchange," *Structure* 2003, 11:1537-1546.

Landis, et al; "Cyclin D1-dependent kinase activity in murine development and mammary tumorigenesis," *Cancer Cell* 2006, 9:13-22.

Liu et al.; "Structural and Functional Analysis of Cyclin D1 Reveals p27 and Substrate Inhibitor Binding Requirements," *ACS Chem Biol* 2010, 5(12); 1169-1182.

Malumbres, et al.; "To cycle or not to cycle; a critical decision in cancer," *Nature Reviews Cancer* 2001, 1:222-231.

McInnes, et al.; "Peptidomimetic design of CDK inhibitors targeting the recruitment site of the cyclin subunit," *Current Medicinal Chemistry—Anti-Cancer Agents* 2003, 3:57-69.

Mendoza, et al.; "Selective Cyclin-dependent Kinase 2/Cyclin A Antagonists that Differ from ATP Site Inhibitors Block Tumor Growth," *Cancer Research* 2003, 63:1020-1024.

Milik, et al.; "Algorithm for rapid reconstruction of protein backbone from alpha carbon coordinates." *J.Comp. Chem.* (1997) 18(1) p. 80-85.

Oelgeschlager, "Regulation of RNA polymerase II activity by CTD phosphorylation and cell cycle control," *Journal of Cellular Physiology* 2002, 190:160-169.

(Continued)

*Primary Examiner* — Fred H Reynolds
(74) *Attorney, Agent, or Firm* — Dority & Manning, P.A.

(57) ABSTRACT

Structural and functional analysis of peptide inhibitor binding to the cyclin D and cyclin A groove has been investigated and used to design peptides that provide the basis for structure-activity relationships, have improved binding and have potential for development as chemical biology probes, as potential diagnostics and as therapeutics in the treatment of proliferative diseases including cancer and inflammation.

5 Claims, 6 Drawing Sheets

(56) References Cited

OTHER PUBLICATIONS

Ray, et al.; "p27Kip1 inhibits cyclin D-cyclin-dependent kinase 4 by two independent modes," *Mol Cell Biol* 2009, 29:986-999.
Russo, et al.; "Crystal structure of the p27Kip1 cyclin-dependent-kinase inhibitor bound to the cyclin A-Cdk2 complex," *Nature* 1996, 382:325-331.
Schulman, et al.; "Substrate recruitment to cyclin-dependent kinase 2 by a multipurpose docking site on cyclin A," *Proceedings of the National Academy of Sciences of the United States of America* 1998, 95:10453-10458.
Sherr, CJ, "Cancer cell cycles," *Science* 1996, 274:1672-1677.
Takai, et al.; "The structure of CDK4/cyclin D3 has implications for models of CDK activation," *Proc Natl Acad Sci U S A* 2009, 106:4171-4176.
Yu, et al.; "Requirement for CDK4 kinase function in breast cancer," *Cancer Cell* 2006, 9:23-32.
Zheleva et al. "Highly potent p21 WAF1-derived peptide inhibitors of CDK-mediated pRb phosphorylation: Delineation and structural insight into their interactions with cyclin A," *J. Peptide Res.*, 2002, 60, 257-270.

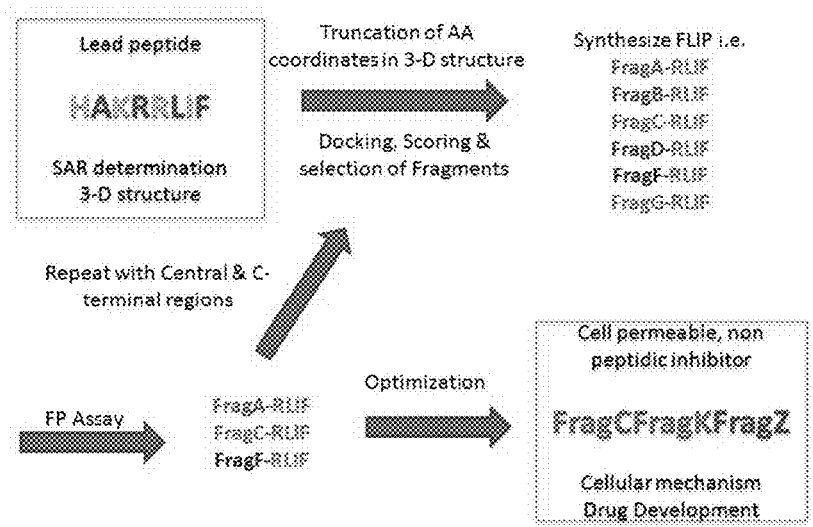
FIG. 1
M210 I213 *L214* D216 W217 E220 V221 *E224* *R250* G251 L253 Q254 Y280 I281 T282 D283 T285
M56 I59 *V60* *T62* W63 E66 V67 *E70* *K96* S97 L99 Q100 I126 Y127 T128 D129 S131
FIG. 2A
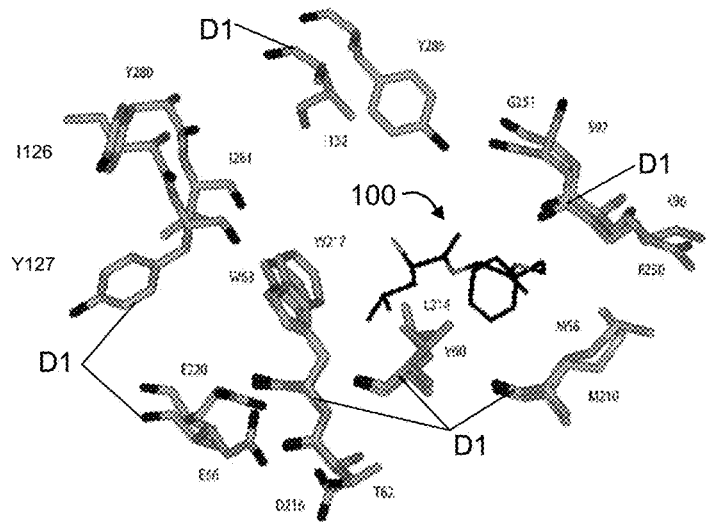
FIG. 2B

CYCLIN BASED INHIBITORS OF CDK2 AND CDK4

CROSS REFERENCE TO RELATED APPLICATION

This application is a continuation application of U.S. patent application Ser. No. 14/492,753 having a filing date of Sep. 22, 2014, now U.S. Pat. No. 9,376,465 having an issue date of Jul. 28, 2016, which is a divisional application of U.S. patent application Ser. No. 13/940,407, having a filing date of Jul. 12, 2013, now abandoned, which is a continuation-in-part application claiming priority to U.S. patent application Ser. No. 13/851,661 having a filing date of Mar. 27, 2013, which claims filing benefit of U.S. Provisional Patent Application Ser. No. 61/616,154 having a filing date of Mar. 27, 2012, all of which are incorporated herein by reference in their entirety.

GOVERNMENT SUPPORT CLAUSE

This invention was made with government support under RO1 CA131368-O1A2 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 24, 2013, is named USC-323_SL.txt and is 16,910 bytes in size.

BACKGROUND

CDKs, the cyclin regulatory subunits and their natural inhibitors, the CDK tumor suppressor proteins (CDKIs), are central to cell cycle regulation and their functions are commonly altered in tumor cells. Deregulation of CDK2 and CDK4 through inactivation of CDKIs such as $p16^{INK4a}$, $p21^{WAF1}$, $p27^{KIP1}$ and $p57^{KIP2}$ may override the G1 checkpoint and lead to transformation. CDKs interact with certain cell cycle substrates through the cyclin binding motif (CBM) and form a complex with the cyclin groove of the G1 and S phase cyclins, a surface binding site involving a protein-protein interaction. It has been shown that CDK isoform and substrate selective inhibition may be achieved through the use of peptides that block recruitment of both pRb and E2F and potently inhibit CDK2/CA kinase activity. Inhibition of CDKs though the cyclin provides an approach to obtain selectivity against other protein kinases and inhibit only the G1 and S phase CDKs as only these contain a functional cyclin binding groove. In particular, CDKs that regulate the RNA polymerase-II transcription cycle should be unaffected by cyclin groove inhibitory (CGI) compounds. Although it has been shown that cancer cells depend on the RNAPII cycle to express anti-apoptotic genes and that inhibition of transcriptional CDKs leads to potent anti-tumor agents, it is at the same time likely that this will lead to effects in normal cells and may be responsible for toxicities observed with current CDK inhibitors being clinically evaluated.

The cyclin binding motif represents a consensus of the cyclin groove binding sequences found in many cell cycle and tumor suppressor proteins. CGI peptides in transducible form have been shown to induce cell cycle arrest and selective apoptosis in tumor cells in vitro. These permeabilized peptides also act as anti-tumor agents in that when administered directly to a SVT2 mouse tumor model, significant tumor growth inhibition was obtained and histological analysis showed that tumors underwent apoptosis.

The ATP competitive CDK inhibitors developed to date are generally non specific against the single variants in the CDK family. It is believed that a major component of the anticancer activity of CDK inhibitors is through the transcriptional inhibition of CDK7 and 9. While it has been suggested that transcriptional CDK inhibition may be beneficial for cancer therapy, it is also probable that this will lead to significant toxicities. The most selective CDK inhibitor described to date is a CDK4, 6 selective compound, PD0332991 (selective vs. CDK2/protein kinases (CDK4 $IC_{50}$, 0.011 µmol/L; Cdk6 $IC_{50}$, 0.016 µmol/L, no activity against 36 other protein kinases) (($IC_{50}$-half maximal inhibitory concentration) although it has apparently not been tested against the transcriptional CDKs. Regardless, this compound is a potent antiproliferative agent against retinoblastoma (Rb)-positive tumor cells and induces a G1 arrest, with concomitant reduction of phospho-Ser780/Ser795 on pRb. Oral administration to mice bearing the Colo-205 human colon carcinoma xenografts resulted in marked tumor regression suggesting that it has significant therapeutic potential and that targeting CDK4/cyclin D may be a viable strategy. In addition to cyclins A and E, the D-type cyclins also contain a functional cyclin groove and CDK4/cyclin D dependent kinase activities may therefore be blocked by cyclin groove inhibitors.

Further oncology target validation for selective inhibition of CDK4/cyclin D has been demonstrated using models of breast cancer and where it was shown that mice lacking Cyclin D are highly resistant to mammary carcinomas induced by erbB-2 oncogene. Further research into the role of Cyclin D in tumor formation made use of a mutant form which binds to CDK4/6 but cannot promote catalytic activity. This kinase-defective Cyclin D/CDK complex results in more evidence of resistance to erbB-2 induced tumorigenesis in mice. Combination of these two studies strongly indicates that Cyclin D1/CDK4 kinase activity is required for erbB-2-driven tumorigenesis and therefore confirms that Cyclin D1/CDK4 is a promising oncology target. While there are several reports of potent and selective inhibitors of the CDK2/cyclin A, E substrate recruitment, with both peptidic and peptidomimetic compounds being identified, room for additional inhibitor development exists. Moreover, very little has been reported with respect to either inhibitors or on the requirements for binding to the cyclin groove of CDK4,6/cyclin D1.

Accordingly, what is needed in the art are methods for development of CDK inhibitors, and in particular CDK/cyclin D and CDK/cyclin A inhibitors.

SUMMARY

A variety of synthetic CDK/cyclin inhibitors are disclosed. The inhibitors inhibit interaction of a complex formed between a CDK protein and a cyclin protein with a substrate of the complex. For example, in one embodiment, the inhibitor can include 1-(3,5-dichlorophenyl)-5-methyl-1H-1,2,4-triazole carboxamide (35DCPT) at the N-terminal, βHomoLeu-NMethylPhe-NH$_2$ at the C-terminal, and a linking group between the N-terminal and the C-terminal, the linking group comprising arginine or an arginine isostere.

In another embodiment the inhibitor can having the following structure:

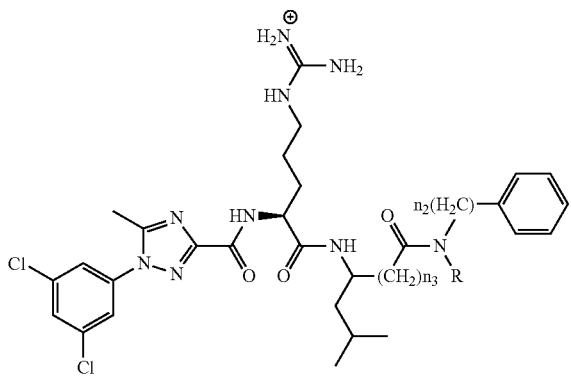

wherein
n1 is 1 or 0,
n2 is 1, 2, or 3,
the aromatic ring bonded to the $(CH_2)_{n2}$ group can include one or more halogens on the ring,
R is hydrogen or ethyl.

In one embodiment, the CDK/cyclin inhibitor can have the following structure:

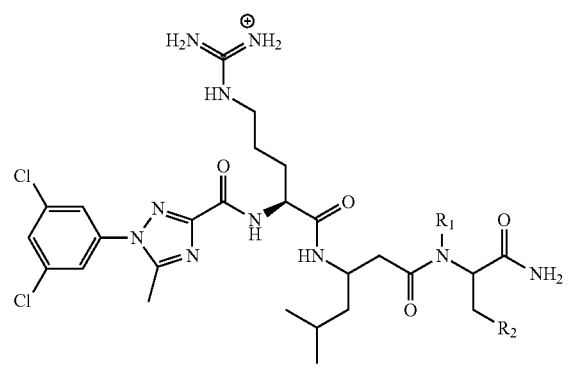

wherein R1 is methyl or hydrogen and R2 has one of the two following structures:

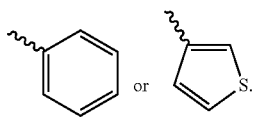

In another embodiment, the inhibitor can have the following structure:

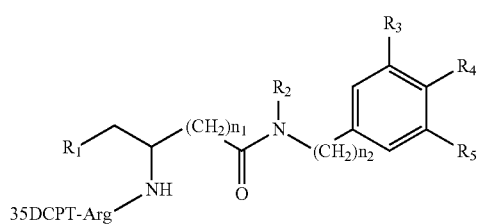

wherein
n1 is 0 or 1,
n2 is 3,
R1 is an arginine side chain
R2 has one of the following structures:

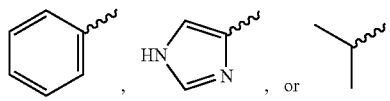

R3, R4, and R5 are independently hydrogen or a halogen.

In yet another embodiment, the inhibitor can be N-(5-guanidino-1-(naphthalen-2-ylamino)-1-oxopentan-2-yl) benzamide.

And in another embodiment, the CDK/cyclin inhibitor includes a terminal C-cap having the following structure:

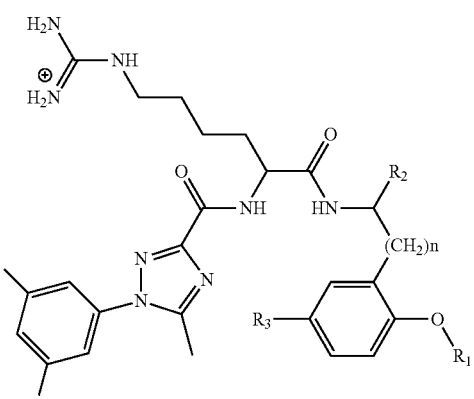

wherein
n is 0 or 1
R1, R2, and R3 are independently hydrogen, isobutyl, methyl, ethyl, or propyl groups.

BRIEF DESCRIPTION OF THE FIGURES

FIG. 1 is a flow diagram illustrating a method as may described herein that may be utilized in development of an inhibitor as described herein. FIG. 1 discloses "HAKRR-LIF" as SEQ ID NO: 2 and "RLIF" as SEQ ID NO: 52.

FIG. 2A is an alignment of binding site residues of cyclin A2 and cyclin D1. FIG. 2A discloses SEQ ID NOS 65 and 66, respectively, in order of appearance.

FIG. 2B illustrates an overlay of crystal structures of cyclin D1 (marked as D1; 2W96) and cyclin A2 (10 KV) illustrating similarities and differences of CBM contacting residues.

DETAILED DESCRIPTION

Figure 2C:
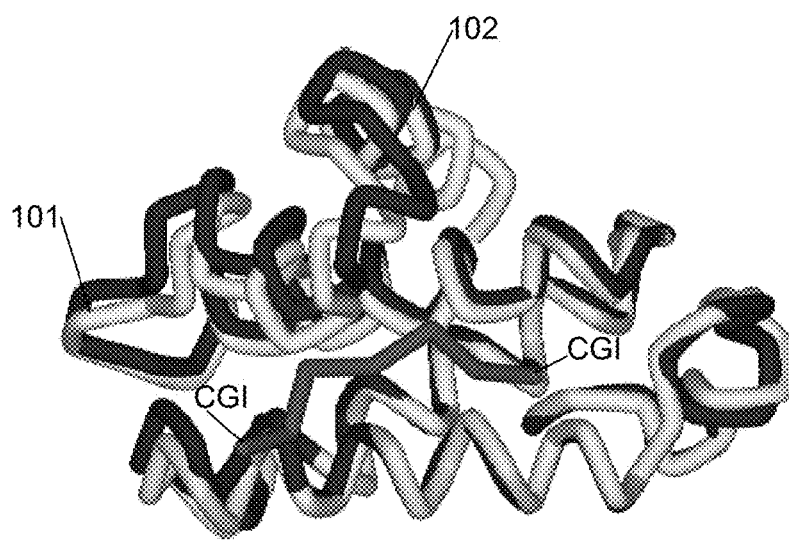
FIG. 2C is a ribbon representation of the overlay highlighting the differences in the cyclin box helices. Cyclin D1 is shown in the lightest strand and the CGI peptide is marked at either end.

The following description and other modifications and variations to the present subject matter may be practiced by those of ordinary skill in the art, without departing from the spirit and scope of the present disclosure. In addition, it should be understood that aspects of the various embodiments may be interchanged in whole or in part. Furthermore, those of ordinary skill in the art will appreciate that the foregoing description is by way of example only, and is not intended to limit the disclosure.

In general, disclosed herein is a strategy for inhibition of the cyclin dependent kinases in anti-tumor drug discovery. More specifically, inhibition may be afforded through the substrate recruitment site on the cyclin positive regulatory subunit. This approach offers the potential of generating cell cycle specific CDK inhibitors and reduction of the inhibition of transcription mediated through CDK7 and 9, commonly observed with ATP competitive compounds. While highly potent peptide and small molecule inhibitors of CDK2/cyclin A, E substrate recruitment have been reported, the development of new CDK2/cyclin A inhibitors would be of great benefit. Moreover, little information has been generated on the determinants of inhibitor binding to the cyclin groove of the CDK4/cyclin D1 complex. CDK4/cyclin D is a validated anti-cancer drug target and it continues to be widely pursued in the development of new therapeutics based on cell cycle blockade.

Synthetic inhibitors disclosed herein have been developed from investigation of the structural basis for peptide binding to the cyclin groove and examination of the features contributing to potency and selectivity of inhibitors. Synthetic inhibitors of CDK4/cyclin D of pRb phosphorylation are disclosed, examples of which have been synthesized, and their complexes with CDK4/cyclin D1 crystal structures have been generated as further described herein. Comparisons of the cyclin grooves of cyclin A2 and D1 are presented and provide insights in the determinants for peptide binding and the basis for differential binding and inhibition.

In addition, a complex structure has been generated in order to model the interactions of the CDKI, p27$^{KIP1}$, with cyclin D1. This information has been used to identify unique aspects of cyclin D1 that have a significant impact on peptide interaction, and which may be exploited in the design of cyclin groove based CDK inhibitors. Peptidic and non-peptidic compounds have been synthesized in order to explore structure-activity relationship for binding to the cyclin D groove and the cyclin A groove which to date has not been carried out in a systematic fashion. Disclosed compounds may be useful as chemical biology probes to determine the cellular and anti-tumor effects of CDK inhibitors that are cell cycle specific and do not inhibit the transcriptional regulatory effects of other cyclin dependent kinases. Furthermore, such compounds may serve as templates for structure-guided efforts to develop potential therapeutics based on selective inhibition of CDK4/cyclin D activity and of CDK2/cyclin A activity.

FIG. 1 is a flow diagram illustrating a method for developing an inhibitor as described herein. According to the process, a lead peptide is selected that is a known inhibitor, e.g., a known cyclin A/CDK peptide inhibitor. By way of example, the octapeptide HAKRRLIF (SEQ ID NO: 2), which is highly selective for cyclin A, can be utilized, as illustrated. The structure activity relationship (SAR) can be determined for the lead peptide inhibitor as can be the 3-D structure for the inhibitor in complex with a cyclin D, e.g., a cyclin D1. A peptidic fragment of the lead peptide can be truncated, for instance an N-terminal fragment, and a substitute segment (either a substitute peptidic fragment or a nonproteinogenic replacement) can then be docked and scored with regard to affinity of the new fragment ligated inhibitor with the cyclin D or with a cyclin A. For example, the substitute segment can be selected via structural analysis of the basis for peptide recognition with the cyclin A and of the decreased potency found in the SAR with the cyclin D, as described further herein. Reiteration and optimization of the fragment can be carried out to determine a best fit fragment replacement segment for the truncated peptidic fragment. The process can then be repeated for the remainder of the original peptide inhibitor, e.g., for a central region of the inhibitor and a C-terminal region of the inhibitor. The combined optimized fragments can then form a new inhibitor for the cyclin/CDK interaction, e.g., the cyclin D/CDK4-substrate interaction, the cyclin E/CDK2 substrate or for the cyclin A/CDK2 substrate interaction.

Common amino acid symbol abbreviations as described below in Table 1 are used throughout this disclosure.

TABLE 1

| Amino Acid | One letter symbol | Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Methods

Solid Phase Peptide Synthesis

Peptides were assembled by using standard solid phase synthesis method on a Argonaut Quest 210 semi-automated solid phase synthesizer. 10 equivalents of the C-terminal amino acid were coupled to Rink resin at the first place using DIEA (0.082 ml) and HBTU (189.6 mg) in 5 ml DMF for 1 h. Fmoc of the C-terminus amino acid was removed using 20% piperidine in 5 ml DMF for 10 mins before assembly of 10 equivalents of the next amino acid using DIEA (0.082 ml) and HBTU (189.6 mg) in 5 ml DMF. Wash cycles (5*10 ml DMF+5*10 ml DCM) were applied to each step in between coupling and deprotection of Fmoc. Upon completion of assembly, side chain protecting groups were removed and peptides were finally cleaved from Rink resin using 90:5:5 mixtures of TFA/H$_2$O/TIS. Crude peptides were purified using reverse phase flash chromatography and semi-preparative reversed-phase HPLC methods. Pure peptides were lyophilized and characterized using mass spectrometry and analytical HPLC. All peptides contained free amino termini and were C-terminal carboxamides.

Computational Chemistry

Modeled complexes of peptidic cyclin groove inhibitors bound to either Cyclin A or Cyclin D were generated as follows: SAKRRLXG (SEQ ID NO: 3) series were modeled from the crystal structure the p107 peptide bound to cyclin A (PDB: 1H28). The HAKRRLIX (SEQ ID NO: 4) series were obtained by hybridizing the peptide conformation of RRLIF (PDB: 10 KV) (SEQ ID NO: 5) and SAKRRLFG (PDB: 1H28) (SEQ ID NO: 6). The Cyclin A structure in this complex was taken from 10 KV. Cyclin D1/SAKRRLXG (SEQ ID NO: 3) and Cyclin D/HAKRRLIX (SEQ ID NO: 4) were generated in a similar manner using cyclin D1 crystal structures (PDB: 2W96) where the peptidic inhibitor bound to cyclin A was superimposed with cyclin D1 and followed by deletion of Cyclin A from further minimization of the complex. After applying the CHARMm forcefield in Discovery Studio 2.5 (Accelrys, San Diego), the Smart Minimizer algorithm comprised of steepest descent and conjugate gradient and an implicit solvent model of Generalized Born with a simple Switching (GBSW) were applied to the complex. In general, all peptide residues were flexible. For cyclin A, all protein residues were restrained and for cyclin D1, the backbone atoms were fixed and approximately 300 steps of minimization were required for convergence to an energy minimum. The calculate interaction energy protocol of DS 2.5 was used to generate non-bonded energy values between peptidic inhibitor and its associated cyclin. This included calculation of van der Waals and electrostatic energies to provide an estimation of the affinity of inhibitors In Vitro Kinase Assay CDK2/Cyclin A2 and CDK4/Cyclin D1 kinase assays were performed using full-length recombinant CDK2/cyclin A2 and CDK4/Cyclin D1 co-expressed by baculovirus in Sf9 insect cells using an N-terminal GST tag on both proteins. The kinase assay buffer I consisted of 25 mM MOPS, pH7.2; 12.5 mM beta-glycerol-phosphate, 25 mM $MgCl_2$, 5 mM EGTA, 2 mM EDTA and 0.25 mM of DTT was added prior to use. The [$^{32}$P]-ATP Assay cocktail was prepared in a designated radioactive working area by adding 150 μl of 10 mM ATP stock solution, 100 μl [$^{32}$P]-ATP (1mCi/100 μl), 5.75 ml of kinase assay buffer I. 10 mM ATP Stock Solution was prepared by dissolving 55 mg of ATP in 10 ml of kinase assay buffer I. Store 200 μl aliquots at −20° C. The substrate used is Rb (773-928) protein with 0.2 mg/ml concentration. The blank control was set up by adding 10 μl of diluted active CDK/Cyclin with 10 μl of distilled $H_2O$. Otherwise, adding 10 μl of diluted active CDK/Cyclin with 10 μl of 0.2 mg/ml stock solution of Rb (773-928). The reaction was initiated by the addition of 5 μl [$^{32}$P]-ATP assay cocktail bringing the final volume up to 25 μl and incubating the mixture in a water bath at 30° C. for 15 minutes. After the incubation period, the reaction was terminated by spotting 20 μl of the reaction mixture onto individual pre-cut strips of phophocellulose P81 paper. The pre-cut P81 strip was air-dried and sequentially washed in a 1% phosphoric acid solution with constant gentle stirring. Radioactivity on the P81 paper was counted in the presence of scintillation fluid on a scintillation counter. The corrected cpm was determined by subtracting the blank control value for each sample and calculating the kinase specific activity as follows: Calculation of [$P^{32}$]-ATP specific activity (SA) (cpm/pmol) Specific activity (SA)=cpm for 5 ul [$^{32}$P]-ATP/ pmoles of ATP (in 5 ul of a 250 uM ATP stock solution). Kinase Specific Activity (SA) (pmol/min/ug or nmol/min/ mg) Corrected cpm from reaction/[(SA of $^{32}$P-ATP in cpm/ pmol)*(Reaction time in min)*(Enzyme amount in ug or mg)]*[(Reaction Volume)/(Spot Volume)] (SignalChem, Richmond, Canada)

Results

Structural Comparison of Cyclin A2 and D1 Binding Grooves

While numerous experimental structures exist for CDK2/ cyclin A2 and other cyclin structures have been solved, for many years CDK4 in complex with the D type cyclins proved refractory to crystallization. The structures for CDK4 in complex with cyclin D1 were recently solved however only in complex with ligands binding to the ATP cleft. This data provided the opportunity to gain new insights into the cyclin groove of the D cyclins and also to determine the basis for their interactions with cyclin groove inhibitory (CGI) peptides. At the outset of this study, a limited body of data had been generated for CDK4 inhibition where a series of peptides explored biologically as CDK2/cyclin A, E inhibitors were also characterized in terms of their inhibition of cyclin D1 mediated substrate recruitment. These results determined that highly potent peptidic CDK2 inhibitors were in general, significantly less potent against CDK4.

In order to determine the structural and functional differences of these compounds, their interactions with the cyclin D1 recruitment site were modeled and compared with known cyclin A complex structures. In terms of cyclin A binding, optimized peptides (i.e. the octamer, HAKRRLIF, p21 sequence (SEQ ID NO: 2)) contain three major determinants which are required for high affinity binding. As illustrated in FIG. 2, these include a primary hydrophobic pocket which interacts predominantly with leucine and phenylalanine residues of the peptide, an acidic region which forms ionic contacts with basic peptide residues and a secondary hydrophobic pocket occupied by either an alanine or valine of the cyclin binding motif (CBM). While the majority of CGI peptide contacting residues are identical or semi-conserved in both cyclin isotypes, two notable exceptions were observed. In cyclin D1, Val60 (interacts with Phe8) and Thr62 (close to Arg4) are substituted for Leu214 and Asp216 in cyclin A2 respectively. As these residues in the cyclin A context, make contacts with major determinants of cyclin A binding, it is expected that even semi-conservative replacements would lead to significant effects on cyclin groove inhibition.

Upon overlay of the corresponding alpha carbons of the two cyclins, other semi-conserved and non-conservative differences were observed in the structural comparison. These residues are not as significant for binding of the octapeptide however their proximity to the cyclin binding groove suggests that they have potential for exploiting in the design of selective CDK inhibitors targeting cyclin D1. Of the non peptide contacting residues, the largest structural variation is in the exchange of Y286 of cyclin A for I132 of cyclin D1. Overlay and comparison of the C-alpha trace of the two structures indicates that this variation, coupled with the relative movement of a helix-loop segment (residues 119-136 of 2W96) leads to a significant conformation variation proximal to the cyclin groove. This region as a consequence is considerably more open in cyclin D1 and provides an extension to the primary hydrophobic pocket. This additional pocket could therefore accommodate larger ligand groups than would be feasible for cyclin A inhibitors.

Sequence alignment of binding sites for cyclin A2 (top) and cyclin D1 (bottom) are shown in FIG. 2A. Residues that contribute to selectivity are shown in italics. The alignment reveals that while a majority of the residues are conserved, Leu214/Val60, Asp216/Thr62, Glu224/Glu70, and Arg250/Lys96 are the main residues that are responsible for selectivity.

FIG. 2B illustrates an overlay of crystal structures of cyclin D1 (2W96) and cyclin A2 (1O KV) illustrating similarities and differences of CBM contacting residues. The Leu and Phe residues of the CBM interacting with the primary hydrophobic pocket are shown at 100. E220 and D216 comprise the acidic region and the secondary hydrophobic pocket is to the left of W217.

FIG. 2C is a ribbon representation of the overlay highlighting the differences in the cyclin box helices. Cyclin D1 is shown as the light ribbon and the ends of the CGI peptide are marked. The region displaying the largest structural differences after superimposing the backbone atoms is marked between 101 and 102 (residues 116-136 of cyclin D1).

Another consequence of the differing conformation and composition of the 116-136 region affects the secondary hydrophobic pocket with which the CGI peptide Ala2 interacts. I281 of cyclin A2 is a Tyrosine residue (Y127) in D1. The kinked helix containing this residue is shifted towards the groove, bringing this residue closer to the peptide and decreasing the volume of the lipophilic pocket on the peptide N-terminal side of the W63 (FIG. 2B).

Structural Basis for Cyclin D1 Inhibition

Prior to detailed analysis of modeled peptide-cyclin D1 complexes, the structural and energetic basis for potencies of cyclin A inhibitors was examined. Since a complete set of cyclin A crystal structures for peptides with cyclin D1 affinity is not available, a cyclin A complex for HAKRRLIF (SEQ ID NO: 2) was first constructed. This peptide is highly selective for cyclin A versus cyclin D1. Formation was completed by building on existing pentapeptide (1O KV) and octapeptide structures to supplement those available for PVKRRLDL (E2F) (SEQ ID NO: 7) and SAKRRLFG (p107) (SEQ ID NO: 6) CBM sequences. The non-bonded interactions of these crystallographic complexes were estimated by calculation of per residue and total interaction energy values (DS 2.5, Accelrys) to determine individual contributions and to establish if these were reflective of the observed affinities (approximated by inhibition constants). These values shown in Table 2, below, delineated a relationship in terms of both previous SAR of individual residues and CGI potency.

TABLE 2

(SEQ ID NOS 2, 6, 7, 5, 8, 2, 6, 7, 5 and 8, respectively, in order of appearance)

| | Cyclin A | | Cyclin A | | Cyclin A | | Cyclin A | | Cyclin A | |
|---|---|---|---|---|---|---|---|---|---|---|
| H | −65.1 | S | −63.9 | P | −23.1 | | | | | |
| A | −18.0 | A | −19.2 | V | −15.8 | | | | | |
| K | −42.2 | K | −40.6 | K | −47.4 | | | | | |
| R | −72.3 | R | −69.7 | R | −74.3 | R | −111.3 | Cit | −38.4 | |
| R | −58.7 | R | −25.2 | R | −9.3 | R | −46.4 | R | −47.2 | |
| L | −11.7 | L | −12.8 | L | −9.9 | L | −13.8 | L | −13.8 | |
| I | −6.8 | F | −12.2 | D | 0.6 | I | −0.1 | I | −0.06 | |
| F | −23.5 | G | −4.2 | L | −15.4 | F | −19.5 | F | −19.5 | |
| Total | −298.3 | | −247.8 | | −194.6 | | −191.1 | | −119.06 | |

| | Cyclin D | | Cyclin D | | Cyclin D | | Cyclin D | | Cyclin D | |
|---|---|---|---|---|---|---|---|---|---|---|
| H | −20 | S | −24.1 | P | −18.8 | | | | | |
| A | −6.3 | A | −5.6 | V | −11.9 | | | | | |
| K | −44.6 | K | −44.7 | K | −52.2 | | | | | |
| R | −54.7 | R | −57 | R | −47.6 | R | −106.9 | Cit | −30.3 | |
| R | −27 | R | −17.6 | R | −11.1 | R | −19.2 | R | −19.2 | |
| L | −15.2 | L | −13.7 | L | −14.7 | L | −14.1 | L | −14.1 | |
| I | 0.7 | F | −10.2 | D | −1.6 | I | 0.2 | I | 0.2 | |
| F | −13 | G | −4.7 | L | −11.7 | F | −13.9 | F | −13.9 | |
| Total | −180.1 | | −177.6 | | −169.6 | | −153.9 | | −77.3 | |

As determined through sensitivity to major potency loss by alanine substitution and other residue replacement, as shown, the energetic analysis shows the critical Arg4 of the octapeptide makes an extensive contribution to binding, whereas that of the less sensitive Arg5 is lower. Truncation of the His-Ala-Lys N-terminal sequence has been previously shown to result in a decreased affinity for cyclin A with the potency decreasing approximately 100 fold. The contribution of these three residues to binding is confirmed through the energetic analysis where His1 and Lys3 especially provide favorable interactions with the binding pocket. The total binding energies of both HAKRRLIF (SEQ ID NO: 2) and RRLIF (SEQ ID NO: 5) calculated (−298 vs −188) correlate well with the inhibition constants of these two compounds. Further analysis of the cyclin residue energetics determined that acidic residues, including Asp216, Glu220, Glu224 and Asp283 allow favorable electrostatic contacts with the basic peptide N-terminal sequence. In addition, the energetics of the contribution of Ala2 to binding correlates well with observed potency increase of the Ser-Ala mutation in the p21 C-terminal context.

Further correlation of the interactions and contributions of the C-terminal sequence of the CBM interacting with the primary hydrophobic pocket (FIG. 2A) in addition to visual inspection of the non-bonded contacts in the p21, p107 and E2F contexts, indicates the structural and energetic differences. In varying peptide sequence contexts, the p21 Leu-Ile-Phe (LIF 'motifette') sequence has been demonstrated to be more potent than the p107 (and p27) LFG and E2F, LDL motifettes. Table 2 illustrates that while the Leucine contributions in each context are similar, the Phe side chain provides increased complementarity in the p21 sequence (−23.5 kcal/mol vs. −12.2) resulting in its 2-3 fold greater affinity compared to the LFG sequence. More favorable contacts are observed due to the geometrical arrangement of the aromatic side chain allowed by the spacer residue between the Leu and Phe in the p21 context. Overall, the energetic analysis of peptide binding to cyclin A confirms that a relationship exists between calculated binding enthalpy and experimental affinity and additionally that individual residue energetics closely correlate with the SAR and contribution of CBM determinants. This relationship provides the basis to perform an analysis of peptide binding to cyclin D1 and to determine the structural basis for decreased affinity of cyclin D1 inhibitors and therefore to facilitate the design of more potent compounds.

The intermolecular complexes of cyclin D1 with the above peptides were formed by superposition of the apo-cyclin D1 structure (2W96) with the crystallographically derived cyclin A bound structure of the CBM containing peptides and followed by deletion of cyclin A. The energy-minimized structure was then calculated using the CHARMm molecular forcefield, and the similarities and differences of cyclin binding motif–cyclin interactions were examined.

Figure 3:
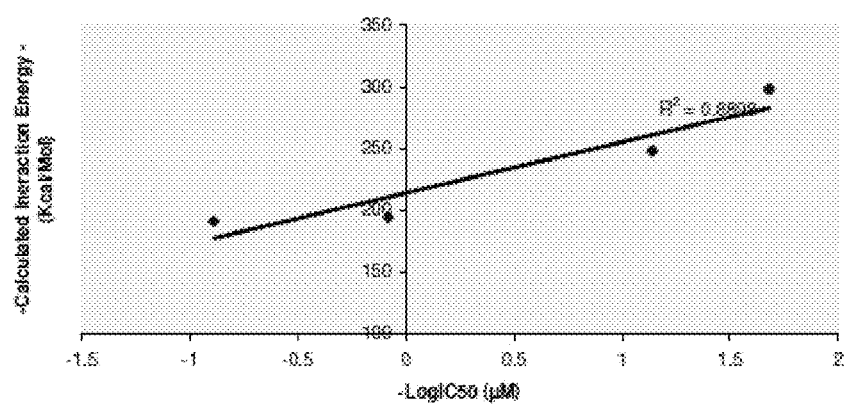
FIG. 3 illustrates a correlation between $IC_{50}$ and interaction energy for several cyclin A-peptide complexes.

In order to further probe the molecular consequences of variations in binding residues, the intermolecular energies were calculated for the interactions of each of the peptides with cyclins A and D1. In line with the observed potencies of each compound and selectivity for cyclin A, a correlation was determined between affinity (kinase inhibition) and total interaction energy (CIE) calculated for 4 peptides ranging in $IC_{50}$ from 0.021 to 99 μM. Results are illustrated in Table 3, below and FIG. 3.

TABLE 3

| Cyclin A | SEQ ID NO: | Interaction Energy (Kcal/Mol) | IC50 (μM) | LogIC50 |
|---|---|---|---|---|
| HAKRRLIF | 2 | −298.3 | 0.021 | −1.68 |
| SAKRRLFG | 6 | −247.8 | 0.073 | −1.14 |
| PVKRRLDL | 7 | −194.6 | 1.2 | 0.08 |
| RRLIF | 5 | −191.1 | 7.7 | 0.89 |

For this relationship, an $R^2$ of 0.91 indicated that the both the crystal and modeled structural complexes were accurate and that the established correlation is useful as a predictive tool for design and synthesis of more potent and selective compounds. Comparison of the predicted affinities of each peptide also demonstrated that the CIE correlates well with the selectivity of the compound for cyclin A (Table 2). This was additionally confirmed by a second method for estimation of binding affinity. Calculation of Ludi Scores provided results directly in line with the relative potencies on A vs. D1. Further analysis of the individual energetic contributions of residues of both the peptide and cyclin in each context revealed further evidence for the structural basis of CGI selectivity. Not surprisingly, it was observed that the cyclin D binding site variations described above contributed extensively to the selectivity of each peptide for cyclin A2. Of course, any inhibitory peptide may be utilized in a modeling process as disclosed herein. In general, the peptide inhibitor will be relatively short, for instance about 10 amino acids or less in length, or about 8 amino acids or less in length, such as the octapeptides, pentapeptides, and tetrapeptides specifically detailed herein.

The optimized p21 derived peptide, HAKRRLIF (SEQ ID NO: 2) is highly selective for A (0.021 μM) vs. D1 (6 μM). In addition to the total interaction energy describing the non-bonded interactions of the peptide-cyclin interaction, the individual contributions of residues from both molecules was determined. These results indicate that the highly basic N-terminal residues interact much more favorably with the cyclin A groove. As no crystal structure is available for this peptide, an A complex was modeled on the basis of the residue contacts of RRLIF (10 KV) (SEQ ID NO: 5) and SAKRRLFG (1H28) (SEQ ID NO: 6). Analysis of protein-peptide contacts and interaction energies reveals that a greater concentration of acidic residues in A2 compared to D1 contributes extensively to this selectivity. In particular Asp216 of cyclin A2 (which is aligned with T62 of cyclin D1) provides a favorable addition of 17 kcal/mol to the binding energy in interactions with Arg4. This contribution is largely absent in the cyclin D1 complexes modeled where the hydroxyl group of T62 weakly interacts with Arg4. When the interaction of both Arg4 and Arg5 are considered, the calculated binding energy of these two residues for cyclin A is more than twice that observed for cyclin D1. Glu220 in Cyclin A2 interacts with Arg4 similarly to the corresponding residue (Glu66) in Cyclin D suggesting that the energetic differences are mainly due to the absence of the second acidic residue in D.

As mentioned above, comparison of the CGI peptide binding residues in cyclin D1 revealed that a valine residue occupied the position observed as a leucine in A2 (Leu214Val). As this residue is located in the lipophilic pocket interacting with the LIF motif of p21, the immediate conclusion is that this contributes significantly to peptide selectivity for A vs D. Initially, this appears to be counter-intuitive since valine is a smaller residue and might be expected to provide a larger binding pocket. Close examination of the position of Val60 indicates that the shorter and less flexible side chain brings the interacting methyl groups closer to the phenylalanine of the peptide and therefore decreases the volume of the hydrophobic pocket (FIGS. 2B, 4B). This was confirmed upon overlay of cyclin A2 bound to HAKRRLIF (SEQ ID NO: 2) with the cyclin D1 modeled complex, where a significant steric clash with the Phe8 side chain was observed (FIGS. 2A, 2B). This suggests that the binding mode of Phe8 with cyclin A2 is not compatible for interaction with cyclin D. In order to determine the consequences of the overlap, the complex formed between cyclin D1 and HAKRRLIF (SEQ ID NO: 2) was subjected to energy minimization to relieve this overlap. A significant displacement of the phenylalanine was observed and which did not come at the expense of Leu6 (peptide residue), whose position was not affected. Further analysis of the interaction energy and comparison with the values calculated for octapeptide inhibition of both cyclins, indicated a reasonable correlation between predicted and calculated per-residue affinity of the C-terminal motifette. These data suggest that displacement of the aromatic side chain comes at the expense of its complementarity with the primary hydrophobic pocket and that the valine substitution is responsible for the significant decrease in affinity for cyclin D1.

Figure 4:
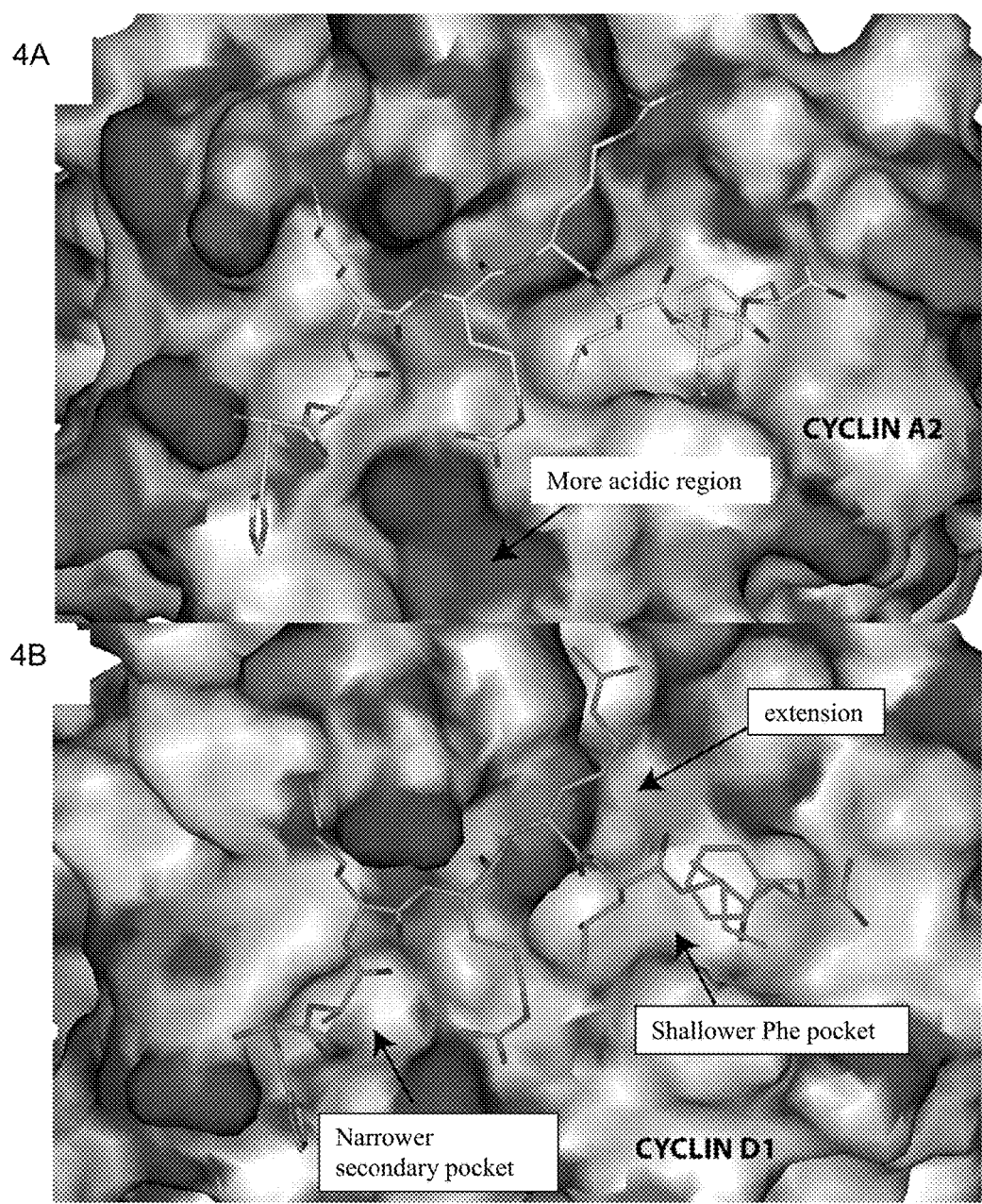
FIG. 4 is a comparison of the solvent accessible surface of the cyclin grooves of A2 (FIG. 4A) and D1 (FIG. 4B).

FIG. 4 is a comparison of the solvent accessible surface of the cyclin grooves of A2 (FIG. 4A) and D1 (FIG. 4B). The individual subsites of the CBG are labeled for each cyclin. Examination of the intermolecular contacts and interaction energies for SAKRRLFG (p107 cyclin binding motif) (SEQ ID NO: 6) with cyclin D1 reveals a similar pattern of residue energetics for the basic region of the peptide as in the HAKRRLIF (SEQ ID NO: 2) context. SAKRRLFG (SEQ ID NO: 6) has a lower affinity for cyclin A, with the less optimal geometry of the LFG motifette resulting in a reduced contact surface area of the phenyl ring with the pocket. Calculation of the individual residue interaction energies suggests that the presence of Val60 has a markedly smaller impact on affinity of the p107 peptide for cyclin D1 than in the p21 context due to the different approach angle of the interacting side chain, and that the selectivity results from increased affinity of the Arg4Arg5 determinant with cyclin A2.

Comparison of the E2F CBM, PVKRRLDL (SEQ ID NO: 7) (Table 3, FIG. 4) reveals further insights into the structural basis for CGI selectivity for cyclin A and after comparison of the binding energetics again indicates less favorable contacts with the peptide in the cyclin D1 context (Table 2). As has been previously described, the LDL containing inhibitors generally have a decreased binding relative to the LIF compounds and in this case is reflected in the 50 fold increased IC50 value. In contrast to the LFG sequence, the LDL sequence has a substantially lower predicted affinity for hydrophobic pocket of cyclin D1, consistent with the observed inhibition constants.

Further Analysis of Peptide SAR and Insights into the Design of Selective Cyclin D1-CDK4 Inhibitors The insights into the structural basis for peptide recognition for cyclin A and for the decreased potency against cyclin D1, provided further opportunity to expand inhibitor structure activity relationships by including additional derivatives. As suggested from the above structural analysis, differences in the primary hydrophobic pocket were the major determinants in cyclin A selectivity of the studied peptides. These observations predicted that analogs with variant C-terminal groups may interact with the cyclin D pocket with differing affinity than to the cyclin A groove. Based on this observation, further peptides were designed to exploit these structural differences and generate compounds with increased affinity for cyclin D1. Due to the decreased volume of the primary pocket in cyclin D1, a series of non-proteinogenic cyclic replacements for Phe7 (p107) and Phe8 (p21) cyclin binding motif containing octapeptides were designed. A series of 5 and 6 membered ring systems were incorporated into the p21 (HAKRRLIX (SEQ ID NO: 4)) and p107 (SAKRRLXG (SEQ ID NO: 3)) contexts (Table 4, below). As shown, these included 2-furylalanine (X1), 2-thienyl alanine (X2), 3-thienylalanine (X3), cyclobutylalanine (X4), cyclopentylalanine (X5), cyclohexylalanine (X6) and 3 and 4 pyridyl alanine residues (X7 and X8) providing for the most part isosteric functionalities mimicking the interactions of the phenylalanine.

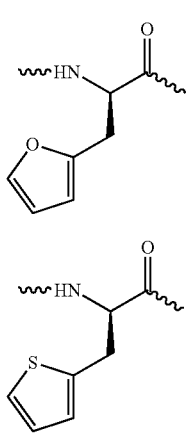

X1

X2

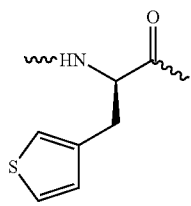

X3

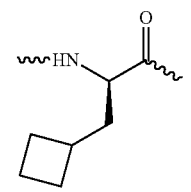

X4

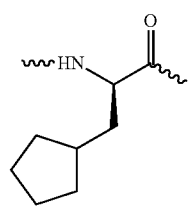

X5

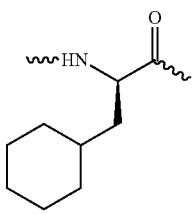

X6

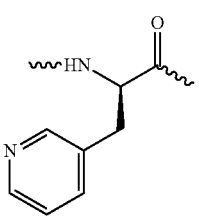

X7

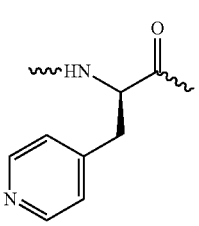

X8

The inhibition of CDK activity was determined through a standard filter capture assay involving a GST-labeled Rb protein and quantification of the incorporation of 32P into the substrate. Activities of peptides previously tested against CDK2A and CDK4D were determined using this assay format. Although similar constructs and substrate was used, significant differences in potency were observed. In particular the IC50 for HAKRRLIF (SEQ ID NO: 2) was approximately 10 fold higher than previously determined (1.3 vs. 0.14 µM) and the inhibition of CDK4/D1 was more pronounced than before (1.6 vs. 6 µM). These differences may be accounted for in slight differences in amount of cyclin in the protein prep and excess cyclin or CDK would result in data variation. As a consequence, it was decided that structure-activity relationships determined using the kinase assay were best interpreted by functional comparisons calculated relative to the native p21 or p107 sequence in each assay. Data is therefore presented as a ratio of each C-terminal and other analogs activity in addition to the IC50s presented for each compound. Results are shown in Table 4, below.

TABLE 4

|     | SEQUENCE | SEQ ID NO: | IC50 CDK2/ A2(µM) | Potency ratio | IC50 CDK4/ D1(µM) | Potency ratio | IC50 CDK2/ E(µM) |
|-----|----------|------------|-------------------|---------------|-------------------|---------------|------------------|
| p107 | SAKRRLFG | 6 | 3.3 | | 2.9 | | |
|     | SAKRRLX1G | 9 | 9.1 | 2.8 | 7.5 | 2.6 | 4 |
|     | SAKRRLX2G | 10 | 27 | 8.2 | 11.4 | 3.9 | |
|     | SAKRRLX3G | 11 | 1 | 0.3 | 6 | 2.1 | |
|     | SAKRRLX4G | 12 | 100 | 30.3 | 74 | 25.5 | |
|     | SAKRRLX5G | 13 | 18 | 5.5 | 28 | 9.7 | |
|     | SAKRRLX6G | 14 | 83 | 25.2 | 36 | 12.4 | |
|     | SAKRRLX7G | 15 | 80 | 24.2 | 51 | 17.6 | |
|     | SAKRRLX8G | 16 | 750 | 227.3 | 143 | 49.3 | |
|     | HAKRRLIF | 2 | 1.3 | | 1.5 | | 0.3 |
| p21 | HAKRRLIX1 | 17 | 6.1 | 4.7 | 11.4 | 7.6 | 1.3 |
|     | HAKRRLIX2 | 18 | 3.6 | 2.8 | 6.5 | 4.3 | |
|     | HAKRRLIX3 | 19 | 25 | 19.2 | 100 | 66.7 | |
|     | HAKRRLIX4 | 20 | 25 | 19.2 | 100 | 66.7 | |
|     | HAKRRLIX5 | 21 | 20 | 15.4 | 90 | 60.0 | |
|     | HAKRRLIX6 | 22 | 58 | 44.6 | 6.3 | 4.2 | |
|     | HAKRRLIX7 | 23 | 29 | 22.3 | 28 | 18.7 | |

For the 2-furylalanine replacement (X1) in the p107 context, it was found that kinase activity induced by this compound decreased a similar amount in both CDK2A (2.8 fold) and CDK4D (2.6 fold) although slightly less so for the latter. In the p21 context more of a differential was observed (4.7 and 7.6 fold decrease respectively). The p107 X2 derivative (2-thienylalanine) data indicates that the potency decrease against cyclin D was considerably reduced (3.9 fold) relative to cyclin A (8.2 fold decrease). A similar differential was observed for the p21 X2 derivative (2.8 vs. 4.3 fold respectively). The X3 amino acid, 3-thienylalanine was found to be less potent than X2 in both p107 and p21 contexts.

Examination of the results for aliphatic cyclic amino acid replacements, including cyclobutyl (X4), cyclopentyl (X5) and cyclohexylalanine (X6), indicated that depending on the CBM context, different selectivity profiles were observed. X4 resulted in dramatic potency decreases in both contexts however significantly more so with cyclin A. Both the p21 and p107 versions incorporating X5, indicate that it is tolerated to a larger degree in binding to cyclin A. Conversely, the p21 derivative of X6 is tolerated to a significantly larger degree in binding to cyclin D1 with only a 4 fold drop-off observed compared to 45 fold with CDK2/cyclin A. If the IC50s of this compound are considered, it is significantly more potent towards CDK4/cyclin D1 than against CDK2/cyclin A (6.3 vs. 58 µM). A similar trend was shown for the p107 X6 sequence although was not as dramatic. An interesting set of results was obtained for the pyridylalanine derivatives where one carbon of the native Phe residue is replaced with nitrogen. A large decrease in activity was observed for these compounds in both p21 and p107 variants. Binding to cyclin D1 for these analogs was again tolerated to a larger degree, especially with the 3-pyridylalanine derivative (X7) in the p107 context. Unexpectedly, the activity of 4-pyridylalanine (X8) incorporated in SAKRRLXG (SEQ ID NO: 16) decreases 200 fold relative to the native sequence in terms of cyclin A but 46 fold in the p21 X8 derivative. Further analysis of the p21 analog binding to cyclin D1 indicates that the X8 containing peptide loses all activity towards CDK4/cyclin D1. The binding of X7 to cyclin D1 decreases 17.6 fold relative to the phenylalanine in the LXG motif and 18.7 fold in the LIX context.

Structure-Activity Relationship for Peptide Binding to Cyclin D1

For the CDK4/cyclin D1/pRb SAR of the Phe replacements in the SAKRRLXG (SEQ ID NO: 3) context, the most potent analog is the furylalanine, X1 derivative with an IC50 of 7.5 µM with X2, the 2-thiophene containing peptide being slightly less potent (11.4 µM). The order of potency is reversed in the p21 CBM since HAKRRLIX2 peptide (SEQ ID NO: 18) has approximately 2 fold greater inhibition than the furylalanine containing peptide (6.5 and 11.4 µM respectively). The 3-thienyl analog X3 undergoes a potency drop off relative to X2 in both contexts. Cyclobutylalanine incorporation into the p107 context retained a level of binding as do HAKRRLIX5 (SEQ ID NO: 21) and SAKRRLX5G (SEQ ID NO: 13) although this is weak relative to the native sequences. The cyclohexylalanine replacement, X6 was of equivalent potency to the thiophene containing peptide in the HAKRRLIX (SEQ ID NO: 22) context, however of notably higher inhibition than the p107 derivative (6.3 µM vs 36 µM). The 3-pyridylalanine peptides (X7) were considerably more significant inhibitors when incorporated C-terminal to the Ile containing spacer residue and which has previously been shown to allow more favorable geometry for binding. The 4-substituted derivative (X8) are weaker binders in both CBM contexts however with 143 µM IC50 observed in the CDK4/cyclin D1 kinase assay for SAKRRLX8G (SEQ ID NO: 16) and no observable activity for HAKRRLIX8 (SEQ ID NO: 24). For the most part, the p21 sequences follow the previously observed trend as being more potent than the p27 and p107 peptides. Two C-terminal analogs however have higher affinity when incorporated with the p107 residues, these being the furylalanine (X1) and 4-pyridylalanine (X8) containing peptides.

Additional insights into cyclin groove interactions in cyclin D1 are provided by C-terminal and other derivatives incorporated into HAKRRLIF (SEQ ID NO: 2). The p-fluorophenylalanine (4FPhe) derivative has been previously shown to significantly increase the inhibitory potential of peptide cyclin A inhibitors with respect to the native residue. In contrast to these results, synthesis and testing of RRLI (4FPhe) (SEQ ID NO: 25) resulted in decreased inhibition of CDK4/cyclin D1 kinase activity (compared to HAKRRLIF (SEQ ID NO: 2), a 160 fold decrease) vs. only a 20 fold decease in CDK2/cylin A activity).

As discussed in above sections, there are differences in the Arg4 interacting residues in cyclin D1 vs. cyclin A2 and that these variations contribute to decreased binding of peptides to cyclin D1. Specifically, cyclin A has two acidic residues that interact with the positively charged side chain compared to only one in cyclin D1. This residue has previously been shown to be critical for cyclin A binding activity. It would therefore be predicted that replacement of the Arg with an isosteric residue would have less of an impact on cyclin D binding. Incorporation of citrullene into p21 to generate peptide, HAKCitRLIF (SEQ ID NO: 26) in order to determine effect on inhibition of cyclin D confirmed that Arg4 is significant for interaction with cyclin D1, as shown in Table 5. The ratio the activities of the Cit and Arg containing peptides in both contexts revealed that its effect on cyclin D1 activity (14 fold potency decrease) was similar to that observed in cyclin A. This result was corroborated by comparison of the activities of citrullene incorporated into pentapeptide, RCitLIF (SEQ ID NO: 27). Compared to the octapeptide sequence, the 5mer potency decreased roughly 120 fold for cyclin A (1.3 vs. 164 µM) and cyclin D1 (1.5 vs. 179 µM).

TABLE 5

| SEQUENCE | SEQ ID NO: | IC50 CDK2/A2(µM) | Potency ratio | IC50 CDK4/D1(µM) | Potency ratio |
|---|---|---|---|---|---|
| SAKRRLFG | 6 | 3.3 | — | 2.9 | — |
| HAKRRLIF | 2 | 1.3 | — | 1.5 | — |
| RRLIpfF | 25 | 26 | 20.0 | 250 | 166.7 |
| HAKCitRLIF | 26 | 18 | 13.8 | 21 | 14.0 |
| HAKTRLIF | 28 | 50 | 38.5 | 25 | 16.7 |
| CitRLIF | 8 | 164 | 126.2 | 179 | 119.3 |
| SCCP10 | | 25 | 19.2 | 8 | 5.3 |
| SCCP 5624 | | >100 | — | 60 | 20.7 |
| SAKRNLFGM | 1 | — | — | 146 | — |
| SAKRNLFG | 29 | — | — | 75 | — |
| SAKRALFGM | 30 | — | — | 68 | — |
| PAKRRLFG | 31 | 8 | — | 6.7 | — |
| PVKRRLFG | 32 | 3 | — | 28 | — |
| PVKRRL3CFG | 33 | 1 | — | 3.2 | — |

Inhibitors are described in Table 6, below. In Table 6, 3TA is 3-thienylalanine, bLeu is betahomoleucine, CHA is cyclohexylalanine, and dimethyllysine is lysine with the epsolon amino group methylated.

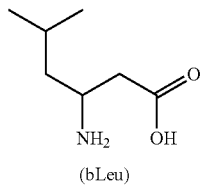

(bLeu)

Insights into SAR for interaction of cyclin D1 inhibitors of the secondary hydrophobic was revealed through synthesis of peptides containing the E2F and p107 CBMs. A preference for smaller side chains was indicated by the increased inhibition of PAKRRLFG (SEQ ID NO: 31) compared to that of PVKRRLFG (SEQ ID NO: 32). This result is in agreement with the structural analysis which shows a decreased volume of this subsite in cyclin D1 compared to A From previous studies into the replacement of peptide determinants with fragment alternatives, compounds were identified where the p21 LIF motif was replaced with a Leu-bis-aryl ether system, while maintaining a similar potency level for cyclin A2 inhibition. A compound was synthesized incorporating 3-phenoxybenzylamide replacing the Phe and also N-terminally capped with 1-(3,5-dichloro-phenyl)-5-methyl-1H-1,2,4-triazole-3-carboxylic acid and subsequently tested for inhibition of CDK4/D1 (SCCP10 on Table 5). SCCP10 was found to have a respectable inhibition of cyclin D1 and in addition, its relative potency compared to the p21 octapeptide was enhanced compared to cyclin A inhibition. SCCP10 is 5 fold less potent than HAKRRLIF (SEQ ID NO: 2) towards cyclin D1, however undergoes a 20 fold drop off when cyclin A2 activity is considered. A similar trend was observed for the SAKRRL-3PBA peptide (SEQ ID NO: 51) small molecule hybrid 3-phenoxybenzylamide end capped peptide when tested against both cyclin grooves although in this context the cyclin A differential was not as profound. Arg-Arg-13-homoleucyl-3-phenoxybenzylamid (SCCP 5624) was also synthesized and shown to be selective for CDK4/cyclin D1.

The Phe side chain of the octopeptide HAKRRLIF (SEQ ID NO: 2) was replaced with smaller side chains in a series of compounds as shown below in Table 6. SCCP396, possessing furyl-Ala replacement was indeed selective for cyclin D1 (15% of kinase activity enhancement for cyclin

TABLE 6

| SCCP ID | Peptide Sequence | SEQ ID NO: | CDK2/cyclin A IC50 (mM) | CDK4/cyclin D1 IC50 (mM) |
|---|---|---|---|---|
| 540 | RRLNpfF | 34 | 0.58 | 8 |
| 5811 | RRLIF | 5 | 1.4 ± 0.42 | 16.1 ± 1.73 |
| 5812 | Cit-RLIF | 8 | 23.7 ± 8.49 | 72.3 ± 11.09 |
| 5831 | RCitLIF | 27 | 6.4 ± 2.76 | 46.5 ± 17.04 |
| 5832 | RPLIF | 35 | ~100 | >180 |
| 5833 | RALIF | 36 | 11.3 ± 3.54 | >100 |
| 5871 | RRLFG | 37 | 19.4 ± 1.77 | >100 |
| 5873 | RGLIF | 38 | 87.0 ± 30.05 | >180 |
| 5874 | RRLF | 39 | 24.8 ± 12.66 | 100~180 |
| 5875 | RR{bLeu}F | 40 | 3.3 ± 2.33 | 20.7 ± 12.45 |
| 5876 | RR{bLeu}FG | 41 | 2.8 ± 0.78 | 22.4 ± 14.57 |
| 5877 | RXLIF X is DMAM peptoid | 42 | >>100 | >>180 |
| 5878 | NNC11-X-LIF DMAM peptoid | | >>100 | >>180 |
| 5879 | RZLIF Z = DMAMAla peptoid | 43 | >>100 | >>180 |
| 457 | SAKRRLFG-NH2 | 44 | 0.30 ± 0.15 | 1.6 ± 0.55 |
| 5815 | SAKRRLFG-OH | 45 | 0.35 ± 0.15 | 1.2 ± 0.38 |
| 5814 | SAKRRL3TA G-OH | 46 | 0.43 ± 0.23 | 3.9 ± 0.55 |
| 5820 | SAKRR{bLeu}FG-OH | 47 | 0.13 ± 0.014 | 0.48 ± 0.090 |
| 5813 | SAKRR{bLeu}3TAG-OH | 48 | 0.31 ± 0.25 | 0.59 ± 0.015 |
| 5816 | HAKRRLI{CHA} | 22 | 0.25 ± 0.21 | 0.26 ± 0.13 |
| 444 | HAKRRLIF | 2 | 0.13 ± 0.035 | 0.22 ± 0.11 |
| 5941 | R{bLeu}NMeF-NH2 | | 0.405 ± 0.091 | 89.65 |
| 5925 | R(NMeArg)LIF | 49 | 13.9 | |
| 5930 | R{bLeu}NMeF | | 0.505 ± 0.36 | 61.17 |
| 5918 | R(dimethyllys)LIF | 50 | 5.4 | 72.2 |

D1 vs. A2). Other replacements with larger ring systems (SCCP 397, 401, 402) were not as favorable. The smaller side chains thus reacted more favorably with cyclin D1.

N-Terminal Partial Ligand Alternatives:

Derivatives and Isosteres of 1-phenyl-1H-1,2,4-triazole-3 carboxamide.

Based upon the above results and other known compounds (see, e.g., Andrews, et al. ChemBioChem, 2006, 7, 1909-1915), the N-terminal Arginine of the p21 RLIF tetrapeptide was substituted with a series of different heterocyclic isosteres capable of interactions similar to critical amino acids of the parent peptide and the triazole. Pyrazole, furan, pyrrole and thiazole systems were synthesized and various substitutions of the phenyl ring were explored. The N-caps were ligated to the tetra peptide using solid phase synthesis, purified by reverse phase HPLC and characterized by MS.

In vitro binding and functional assays were performed in order to study the inhibitory effect of compounds on CDK2/Cyclin A prior to further evaluation in cell viability assays to determine antitumor effects. On the basis of the results, further high throughput docking of potential heterocyclic fragments was carried out to identify N-capping groups of varying chemical diversity for synthesis and in vitro testing.

A phenyl 1,2,4-triazole series (Scaffold I) was utilized as a basis for development of a family of phenylheterocylcic compounds as potential N-capping groups for cyclin A and/or cyclin D inhibitors. The general structure of the compounds was:

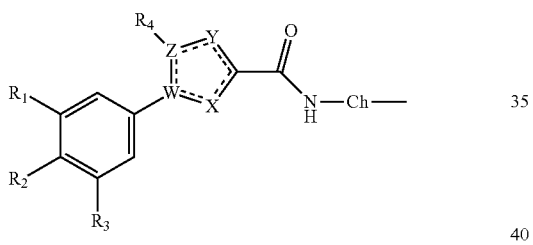

wherein $R_1$, $R_2$, $R_3$, $R_4$ are independently hydrogen, halogen, methyl, or methoxy and W, X, Y, and Z are independently C, N, O, or S.

Compounds containing the 1-phenyl-1H-pyrazole-3-carboxamide substructure were synthesized as a potential scaffold and are described in Table 7, below. The synthesis was achieved through a scheme in which ethylacetopyruvate was condensed with the corresponding substituted phenyl hydrazine. Initial attempts involved base catalysis of the reaction upon which two isomers were obtained. The desired isomer was identified and confirmed through 1-D NOE analysis where irradiation of the R4 methyl group led to an enhancement of the two ortho aromatic hydrogens. This reaction was further optimized by performing the cyclization in acidic conditions thereby protonating the hydrazine and suppressing formation of the non-desired regioisomer. The versatile pyrazole synthesis allowed generation of a variety of analogs including the unsubstituted phenyl, the 3-methoxy and 4-methoxy phenyl as well as the 3,5 dichloro, 3 chloro and the 4 chlorophenyl compounds.

The triazole core structure of 1-(3,5-dichlorophenyl)-5-methyl-1H-1,2,4-triazole-3-carbonyl was replaced with isosteres such as pyrazole, furoic acid, pyrrole, and thiazole appropriately substituted with a carboxylic acid group and a phenyl ring. Multiple capping groups were synthesized and ligated with the tetra peptide RLIF (SEQ ID NO: 52). The synthetic schemes for pyrazoles, furan and pyrroles are outlined in scheme 1a, 1b and 1c respectively.

Scheme 1a:

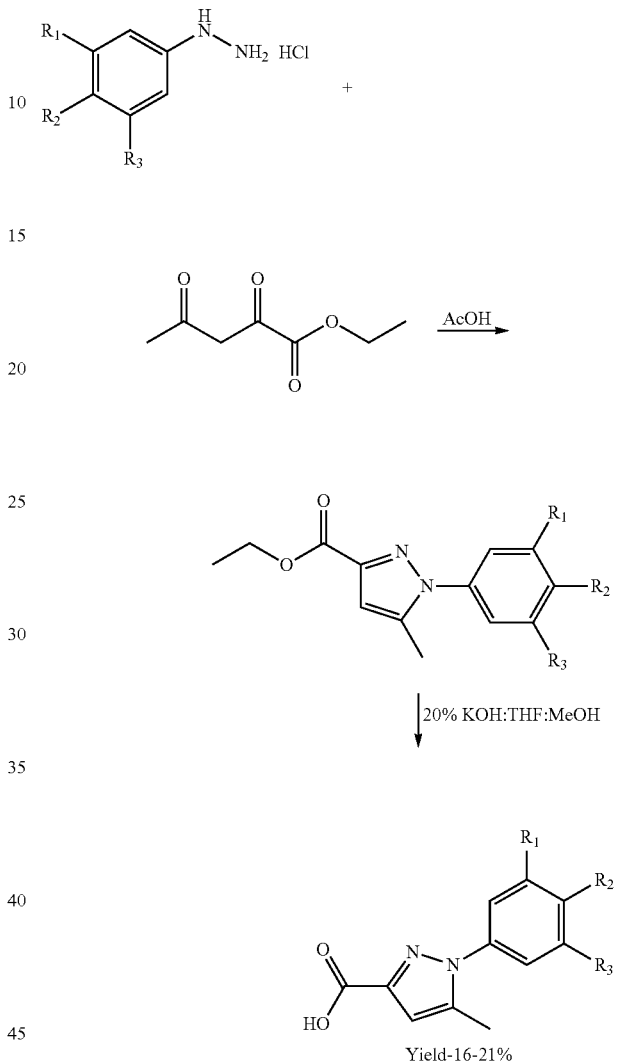

Scheme 1b:

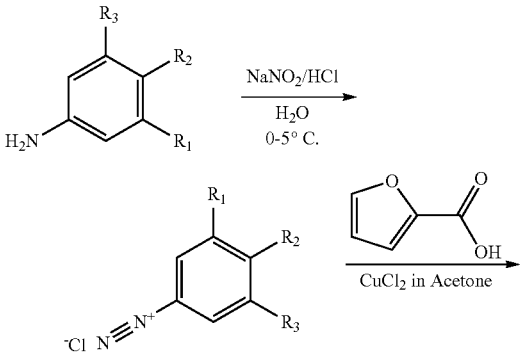

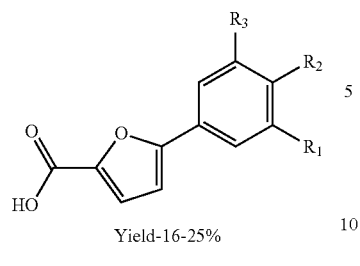

Yield-16-25%

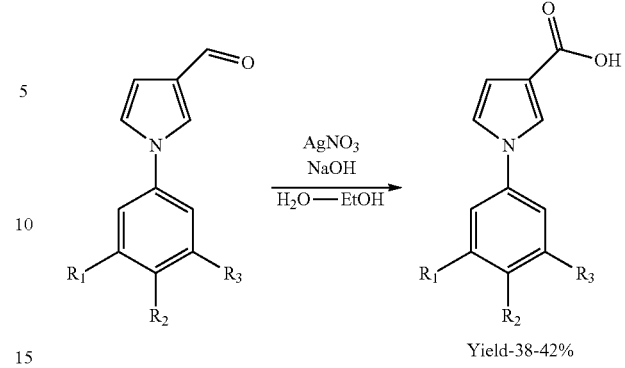

Yield-38-42%

Scheme 1c:

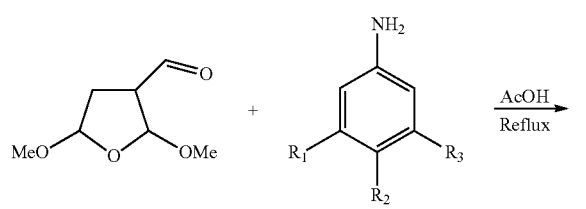

The X-ray crystal structure of (1-(3,5-dichlorophenyl)-5-methyl-1H-1,2,4-triazole-3-carbonyl-RLIF (SEQ ID NO: 53) shows that the N-cap hydrogen bonds with Trp217 and Gln 254 of cyclin A. SAR information in Table 6, below reveals the following:

Triazole N-caps were found to be the most potent of the tested compounds, followed by pyrazole and furan. The 4-chloro substitutions on the phenyl ring are the most effective, followed by 3,5-dichloro substituted compounds.

Pyrrole and thiazole show significantly lower activity than the triazole Ncaps.

TABLE 7

| | SCCP ID No. | $R_1$ | $R_2$ | $R_3$ | $R_4$ | W | X | Y | Z | CDK2/cyclin A $IC_{50}$ (mM) | CDK4/cyclin D1 $IC_{50}$ (mM) |
|---|---|---|---|---|---|---|---|---|---|---|---|
| Triazole | 5843 | H | H | H | H | N | N | N | C | 16.2 ± 3 | 48.7 |
| | 5773 | Cl | H | Cl | $CH_3$ | N | N | N | C | 4 ± 0.6 | 27 |
| | 5774 | H | Cl | H | $CH_3$ | N | N | N | C | 11.5 ± 3.3 | 11.3 |
| Pyrazole | 5762 | H | H | H | $CH_3$ | N | N | C | C | 40.3 ± 6.5 | 53.8 |
| | 5763 | Cl | H | Cl | $CH_3$ | N | N | C | C | 21.8 ± 13.7 | 100~180 |
| | 5764 | Cl | H | H | $CH_3$ | N | N | C | C | 11.9 ± 2.0 | 45 |
| | 5771 | F | H | H | $CH_3$ | N | N | C | C | 29.6 ± 12.2 | 69.6 |
| | 5765 | H | Cl | H | $CH_3$ | N | N | C | C | 33.7 ± 8.1 | 49 |
| | 5766 | $OCH_3$ | H | H | $CH_3$ | N | N | C | C | 64.1 ± 4.2 | 100~180 |
| | 5767 | H | $OCH_3$ | H | $CH_3$ | N | N | C | C | >180 | >180 |
| Pyrrole | 5776 | H | Cl | H | H | N | C | C | C | >180 | >180 |
| | 5775 | Cl | H | Cl | H | N | C | C | C | >180 | >180 |
| Furan | 5768 | Cl | H | Cl | H | C | O | C | C | >180 | >180 |
| | 5769 | Cl | H | Cl | H | C | O | C | C | >180 | >180 |
| | 5772 | F | H | H | H | C | O | C | C | >180 | >180 |
| | 5770 | H | Cl | H | H | C | O | C | C | >180 | >180 |
| | 5588 | $OCH_3$ | H | H | H | C | O | C | C | >180 | >180 |
| | 5587 | $CH_3$ | H | H | H | C | O | C | C | >180 | >180 |
| Imidazole | 5760 | H | H | H | $CH_3$ | C | N | C | N | >180 | >180 |
| | 5852 | F | H | H | H | C | N | C | N | 34.3 ± 0.6 | 67 |
| Thiazole | 5583 | H | Cl | H | H | C | N | C | S | >180 | >180 |

Structures for certain of the capping groups of Table 7 are as follows:
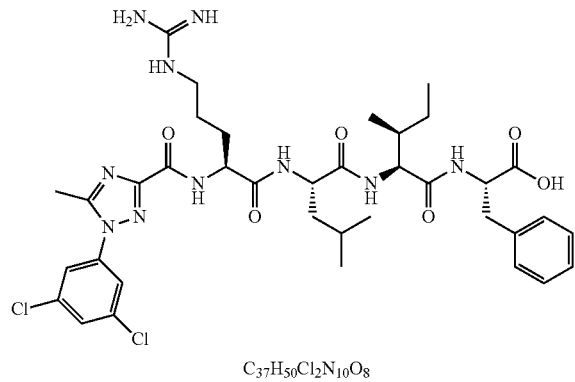
SCCP ID 5773
C$_{37}$H$_{50}$Cl$_2$N$_{10}$O$_8$
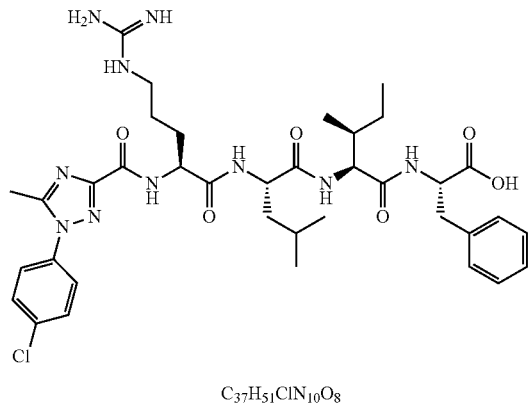
SCCP ID 5774
C$_{37}$H$_{51}$ClN$_{10}$O$_8$
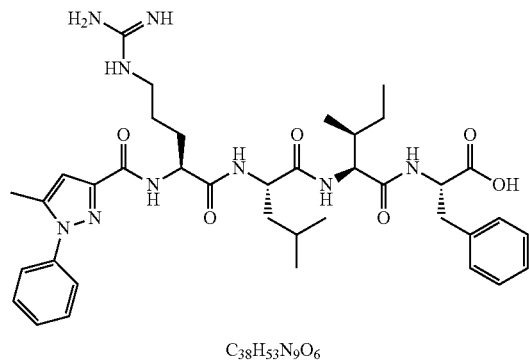
SCCP ID 5762
C$_{38}$H$_{53}$N$_9$O$_6$
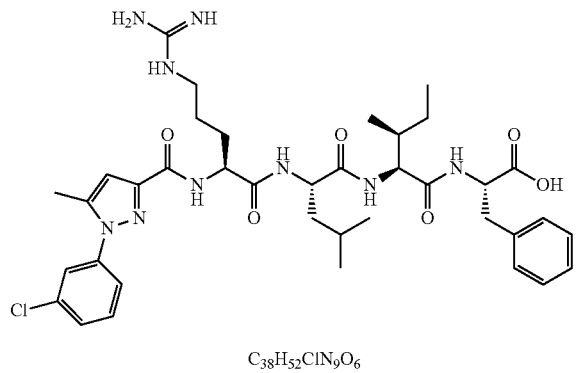
SCCP ID 5764
C$_{38}$H$_{52}$ClN$_9$O$_6$
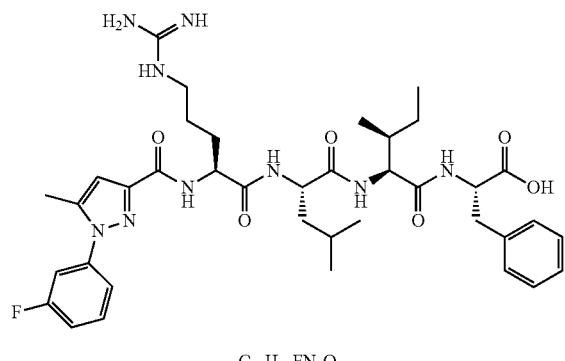
SCCP ID 5771
C$_{38}$H$_{52}$FN$_9$O$_6$
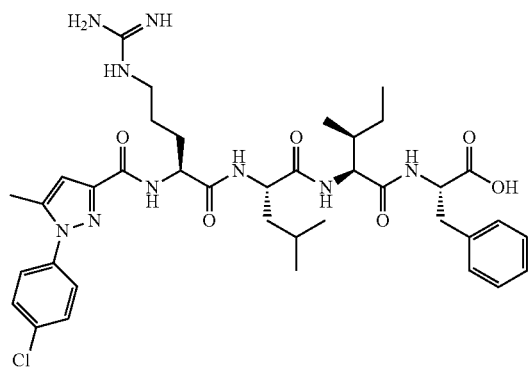
SCCP ID 5765
C$_{38}$H$_{52}$ClN$_9$O$_6$ -continued
SCCP ID 5766
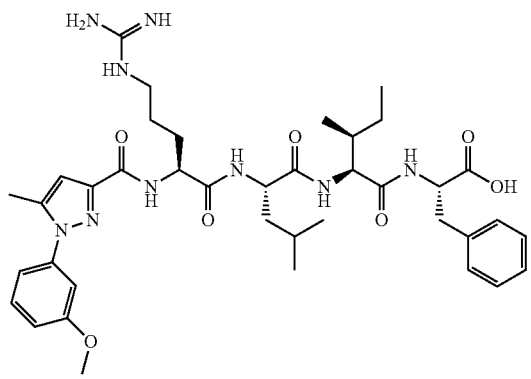
C₃₉H₅₅N₉O₇
SCCP ID 5776
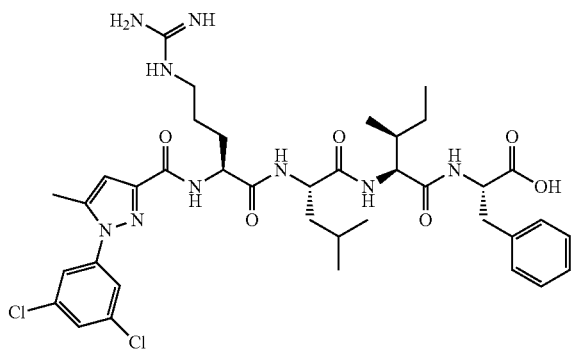
C₃₈H₅₀Cl₂N₈O₆
SCCP ID 5775
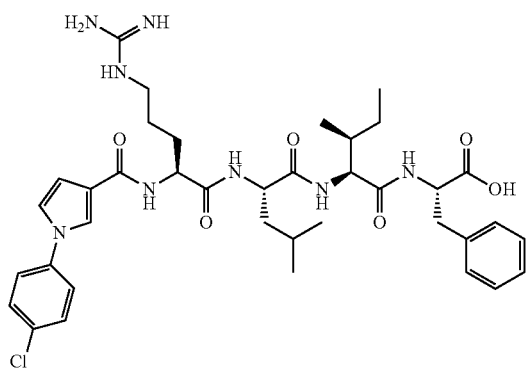
C₃₈H₅₁ClN₈O₆
SCCP ID 5768
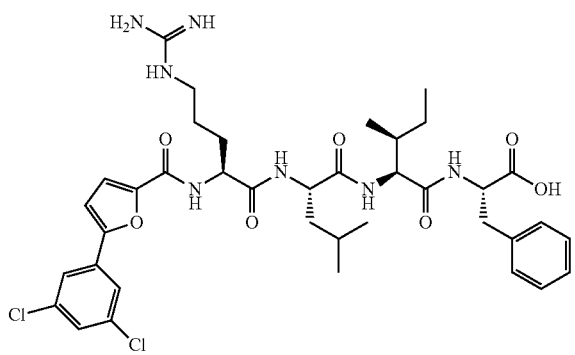
C₃₈H₄₉Cl₂N₇O₇
SCCP ID 5772
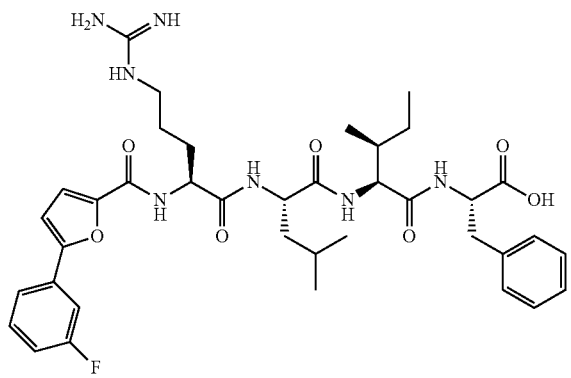
C₃₈H₅₀FN₇O₇
SCCP ID 5770
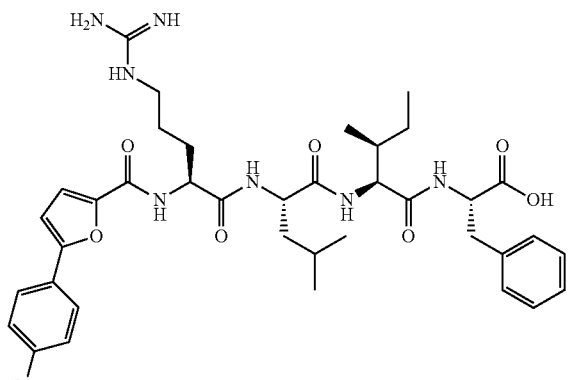
C₃₈H₅₀ClN₇O₇

SCCP ID 5588
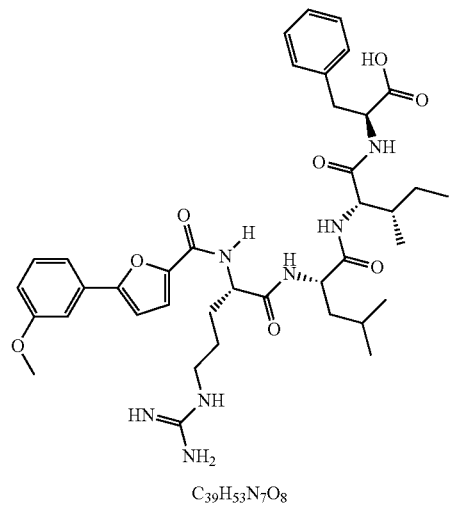
C₃₉H₅₃N₇O₈
SCCP ID 5587
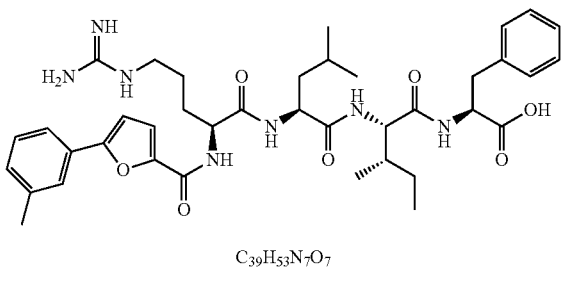
C₃₉H₅₃N₇O₇
SCCP ID 5583
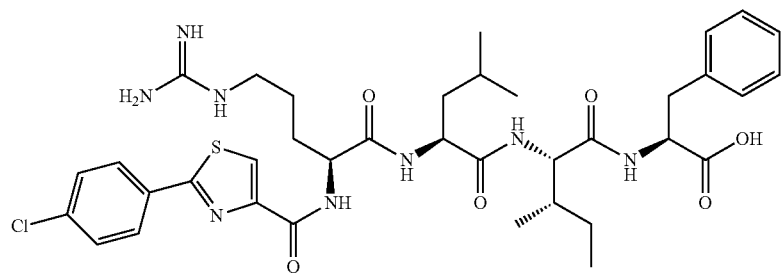
C₃₇H₄₉ClN₈O₆S
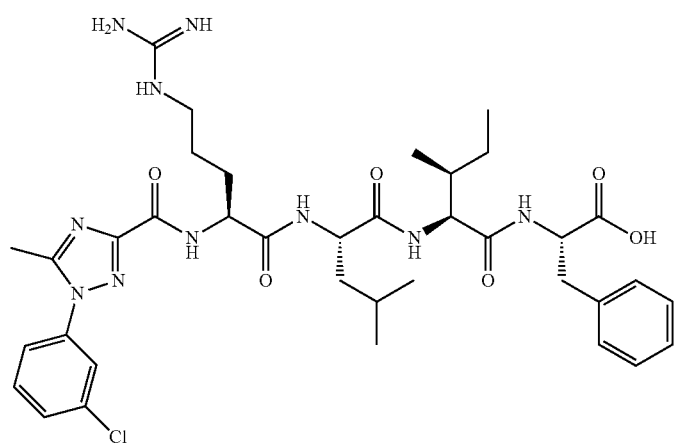 [SMILES: CC[C@H](C)[C@H](NC(=O)[C@H](CC(C)C)NC(=O)[C@H](CCCNC(=N)N)NC(=O)c1nc(C)n(-c2cccc(Cl)c2)n1)C(=O)N[C@@H](Cc1ccccc1)C(=O)O]

By inference in comparing 5763 5764 and 5773, the above compound is believed to have increased activity compared to 5773 (i.e. <4 µM).

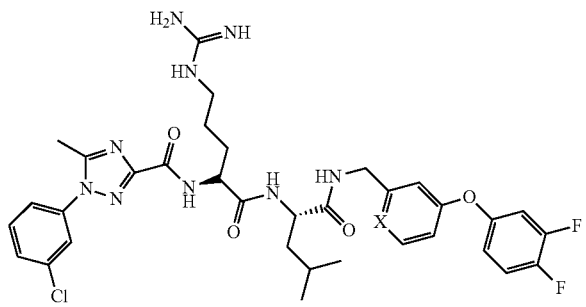

The above compound is believed to have an activity of <5 mM, inferred from the using the best triazole Ncap (above) and also combining the additive effects of the 3 and 4 fluoro subsitutions on the 3-phenoxy(pyridinyl-2-yl)methylamine system.

The series of heterocycles of Table 7 included incorporation of 5-phenylfuran-2-carboxylic acid, 1-phenyl-1H-pyrrole-3-carboxylic acid, and 4-phenylthiazole-2-carboxylic acid in order to interrogate structure-activity of the 5 membered ring. This enabled determination of the consequences of replacing the bridging atom between the phenyl and carboxylic acid substitutions and also to probe the contribution of the 5-methyl substituent in the pyrazole and triazole contexts.

Crystal structures of the 3,5 dichlorophenyl and the 4 chlorophenyl triazole were solved and provided insights into the protein-ligand interactions of this N-terminal PLA. These included increased complementarity of the 3-chloro with the secondary hydrophobic pocket relative to the 4-chloro substitution, a hydrogen bond acceptor from the 2-nitrogen of the 1,2,4-triazole to Trp217 NH and contribution of an additional H-bond acceptor from the amide carbonyl to the carboxamide side chain of Gln254. In order to assess the contribution of the PLA H-bond acceptor, analogous compounds were made in each series and activities for the 4-chloro and 3,5-dichloro analog were evaluated in each context. The resulting SAR around the heterocyclic scaffolds determined that while isosteric ring systems are presented, significant differences are observed in the in vitro potencies as measured in the fluorescence polarization (FP) binding assay.

The triazole containing N capping group was found to act as the best scaffold, followed by the pyrazole, furan and triazole substructures respectively. These differences are manifest in In the CDK4/cyclin D1 context, the fragment ligated inhibitory peptide that was capped with the 4-chlorophenylpyrazole was found to be at least 4 fold less active relative to the triazole N capping group. SCCP ID No. 5770, possessing a furan core structure, was found to be 25 fold less potent in this assay. The two pyrrole containing structures were found to be completely inactive in the binding assays. Comparisons of the 3,5 substituted phenylheterocyclic derivatives revealed a similar trend in binding to the 4-chloro versions. With the relative potencies of the heterocyclic framework established, the versatility of the phenylpyrazole and phenylfuran carboxylic acid syntheses was exploited in order to generate more diverse substitutions. In particular, 3-Cl, 3-F, 3 and 4 methoxy, 3 methyl and unsubstituted phenyl rings were incorporated. Results from the pyrazole context suggested that beneficial substitutions include the 3-Cl, 3-F and 3-H on the phenyl ring. The most potent compounds in the furan isostere included the 3-Me which is 2 fold more potent than the 4-Cl (the most active compound in this series). One imidazole (5-methyl-2-phenyl-2H-imidazole-4-carboxamide) and 2-(4-chlorophenyl)thiazole-4-carboxamide were incorporated on to the peptide, however these were found to possess little activity as N capping groups. Another imidazole derivative, 2-(3-fluorophenyl)-1H-imidazole-4-carboxamide was synthesized, ligated to the RLIF tetrapeptide to form a fragment ligated peptide, and found to have similar activity to the pyrazole core structure.

A method for forming phenyl triazoles (e.g., SCCP ID Nos. 5843, 5773 and 5774) is given in 3-steps below. The particular procedure is for the synthesis of the N-cap for compound 5773, and a similar procedure may be utilized for other phenyl triazoles as will be evident to one of ordinary skill in the art:

Step 1. Procedure to make (E)-ethyl 2-chloro-2-(2-(3,5-dichlorophenyl)hydrazono)acetate 1. Add 10 ml of 6N HCl to a solution of 3,5-dichloroaniline in 10 mL of MeOH at 0 degree C.
2. Sodium nitrite is added slowly
3. Stir reaction for 15 minutes at 0 degree C.
4. Sodium acetate is added to adjust the pH to 5
5. A solution of ethyl 2-chloro-3-oxobutanoate (ethyl 2-chloroacetoacetate) in 10 ml of MeOH is added slowly at 0 degree C.
6. Bring to room temperature and stir the reaction for 12 hours
7. Remove the MeOH under reduced pressure and add diethyl ether
7. Separate and wash the organic layer with saturated sodium bicarbonate and water
8. Dry over sodium sulfate Step 2. Procedure for ethyl 5-methyl-1-(3,5-dichlorophenyl)-1H-1,2,4-triazole-3-carboxylate 1. Prd from step 1. and acetaldehyde oxime are dissolved in toluene and heated to reflux
2. Moniter rxn by TLC
3. Once TLC shows consumption of half of the starting material, additional 0.5 EQ of TEA is added and refulxing is continued
4. Moniter rxn by TLC
5. Rxn is concentrated and partitioned between EtOAc and $H_2O$
6. Layers are separated and the aqueous layer is washed with EtOAc
7. THe combined organics are washed with $H_2O$ and brine
8. Dry with Na2SO4 and filter
9. Then concentrate
10. Crystalize with Et2O (ethyl ether anhydrous) and hexane Step 3. Procedure to make 5-methyl-1-(3,5-dichlorophenyl)-1H-1,2,4-triazole-3-carboxylic acid 1. Add 13.3 mL of Ethanol and 13.3 mL of $H_2O$ to product from Step 2.
2. Reflux the contents for ~2 hrs
3. Evaporate the ethanol
4. Add $H_2O$ and extract with EtOAc 5. Acidify with 1N HCl to ppt the prdt; if the prdt does not ppt, extract aqueous layer with EtOAc 2-3 times, combine EtOAc wash and wash with brine and dry with NA2SO4

Several additional analogs were synthesized in addition to the 3,5 dichloro and 4-chlorophenyl analogs. In addition to determining their inhibition of CDK2/cyclin A, the availability of the CDK4/cyclin D1 binding assay was exploited to develop SAR for both kinases. Interestingly, the relative potencies of the 4-chloro and 3,5-dichlorophenyl triazole (25 and 12 µM for CDK2/cylin A respectively) were reversed in the CDK4/cyclin D1 context (11 and 27 µM). This is the result of different requirements of the secondary hydrophobic pocket in the two cyclins as previously delineated through the study of the binding of peptide analogues.

Validation was carried out to ensure that the method was efficient to produce reproducible results and to show that the docking results of the unknown compounds were predictive. Two native ligands (1-(3,5-dichlorophenyl)-5-methyl-1H-1,2,4-triazole-3-carbonyl and 1-(4-chlorophenyl)-5-methyl-1H-1,2,4-triazole-3-carbonyl) and a negative control were docked in both the sub units A and B of CDK2/Cyclin A crystal structure. The variation in the parameters (i) energy grid (Dreiding, CFF and PLP1), (ii) minimization sphere (on or off) and (iii) number of poses generated (20, 10 and 5) was carried out.

For each parameter, the number of correct poses (poses that are superimposible with the crystal structure binding mode) of the positive control ligands generated, the number of negative control poses in top 25 poses, the best scoring functions that gave more number of correct poses in top ranking order were studied. The optimized parameters are energy grid PLP1 with minimization sphere on and number of poses 10 and the scoring function PLP1. The docking of the native ligands were reproducible with the optimized parameters. The results are shown in Table 8.

3. Spacer between two rings
4. Spacers before the carbonyl group.

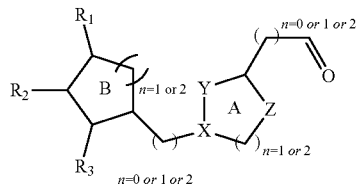

X = N, C, Y = N, S, Z = N, O, NH

R—Cl, F, OCH3

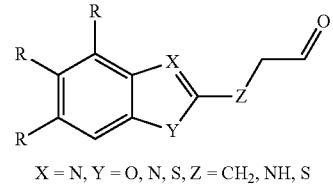

X = N, Y = O, N, S, Z = CH$_2$, NH, S

R—Cl, F, OCH3

Other scaffold series were utilized as a basis for development of the synthetic inhibitors in addition to the 1,2,4-triazole series discussed above. Scaffolds included the following:

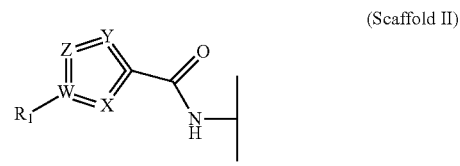

(Scaffold II)

TABLE 8

| Energy Grid | Dreiding | CFF | PLP1 |
|---|---|---|---|
| No. of correct poses 3,5-DCPT | 2 | 4 | 6 |
| No. of correct poses 4-DCPT | | | 8 |
| Negative controls in top 25 | −PLP1(4), −PLP2(4), Jain (4), PMF(4), DOCK SCORE(6) | −PMF (7), DOCK SCORE (6) | No −ve control poses in all the scoring functions |
| Best scoring function | LigScore2_Dreiding | PLP1, PLP2 | PLP1, PLP2 |
| 3,5-DCPT (rank of top 25 correct/closer poses for the best scoring function | 4, 5 (for all the scoring functions) | PLP1 (9, 10, 11, 12, 25), PLP2 (13, 14, 15, 16, 25) | PLP1 (7, 8, 9, 10, 14, 11, 12, 13, 25), PLP2 (11, 12, 13, 14, 18, 15, 16, 17) |
| 4-DCPT (rank of top 25 correct/closer poses for the best scoring function) | | PLP1 (1, 2, 3, 4, 5, 6, 7, 8), PLP2 (17, 18, 19, 20, 21, 22, 23, 24) | PLP1 (1, 2, 3, 4, 5, 6) PLP2 (20, 21, 22, 23, 24, 25) |

Molecules may be designed on the basis of one or more of: (i) Molecular weight less than 250, (ii) absence of charge on the molecules to improve permeation, (iii) Presence of a carboxylic acid group which is essential for ligation to the peptide and (iv) Commercial availability and synthetic feasibility.

Various N-capping group designs are shown below. The scheme for development of the designs generally includes:

1. Ring A is replaced with 5 membered or six membered heterocycles
2. Ring B was replaced with phenyl group or heterocycles -continued

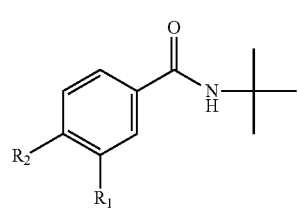

(Scaffold III)

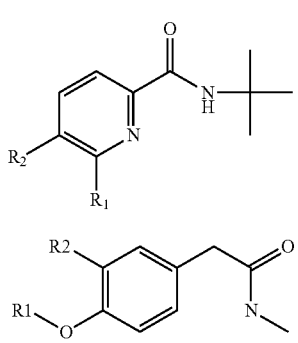

(Scaffold IV)

(Scaffold V)

Examples of capping groups and calculated structure activity for each of the scaffold groups are further described in Table 9 (furans and thiazoles, Scaffold II), Table 10 (benzoic acids, Scaffold III), Table 11 (picolinic acids, Scaffold IV), and Table 12 (phenyl acetic acids, Scaffold V), presented below.

TABLE 9

| SCCP ID | R1 | W | X | Y | Z | CDK2/ cyclin A IC$_{50}$ (mM) | CDK4/ cyclin D1 IC$_{50}$ (mM) |
|---|---|---|---|---|---|---|---|
| 5581 | CH$_2$N (CH$_2$CCH$_3$)$_2$ | C | C | C | C | 47.1 ± 19.2 | 40.7 |
| 5585 | CH$_2$-imidazole | O | C | C | C | 100~180 | 158.8 |

TABLE 9-continued

| SCCP ID | R1 | W | X | Y | Z | CDK2/ cyclin A IC$_{50}$ (mM) | CDK4/ cyclin D1 IC$_{50}$ (mM) |
|---|---|---|---|---|---|---|---|
| 5586 | CH$_2$-pyrazole | O | C | C | C | 100~180 | >180 |
| 5589 | CH$_2$-methylpiperazine | O | C | C | C | >180 | 47.1 |
| 5761* | CH$_2$-4methylpyrazole | O | C | C | C | 100~180 | >180 |
| 5582* | 3-thienyl | C | N | C | S | 70.7 ± 18.6 | >180 |
| 5584 | 2-thienyl | C | N | C | S | >180 | >180 |

As can be seen, the benzoic acid derivatives (Scaffold III, Table 10) gain more potency with substitutions on both the R$_1$ and R$_2$ positions as compared to unsubstituted benzoic acid. At the R$_1$ position, substitutions such as meoxy and phenoxy improve the potency of the compound by more than 2-fold, while at the R$_2$ position, the four substitutions introduced in Table 10 greatly enhance the activity by 26, 9, 3, and 3 fold, respectively. In addition, the presence of basic groups on the four structures suggests that the basic groups are important for binding to cyclin D.

TABLE 10

(Table 10 discloses "RLIF" as SEQ ID NO: 52, "RLNpfF" as SEQ ID NO: 54, "X-RLIF" as SEQ ID NO: 55 and "ALIF" as SEQ ID NO: 56)

| SCCP ID | R1 | R2 | Peptide link | IC50 (μm) CDK2/A2 | CDK4/D1 |
|---|---|---|---|---|---|
| 5857 | H | H | RLIF | >100 | 100-180 |
| 5835 | CH$_3$ | H | RLNpfF | Lost | ~200 (LIF) |
| 5858 | C$_2$H$_6$O | H | RLIF | >100 | 49, 33.9 μm (0321) |
| 5844 | (isobutyl-O-) C$_5$H$_{12}$O | H | RLIF | >100 | >180 |
| 5846 | (phenyl-O-) C$_7$H$_8$O | H | RLIF | >180 | >100 |
| 5882 | (ethyl-O-) C$_3$H$_8$O | H | RLIF | >100 | >100 |
| 5883 | (propyl-O-) C$_4$H$_{10}$O | H | RLIF | >100 | >100 |

TABLE 10-continued
(Table 10 discloses "RLIF" as SEQ ID NO: 52, "RLNpfF" as
SEQ ID NO: 54, "X-RLIF" as SEQ ID NO: 55 and "ALIF" as SEQ ID NO: 56)
| SCCP ID | R1 | R2 | Peptide link | IC50 (μm) CDK2/A2 | IC50 (μm) CDK4/D1 |
|---|---|---|---|---|---|
| 5851 | H | 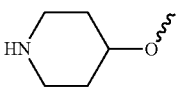 $C_6H_{13}NO$ | RLIF | 32.8 ± 13.5 | 3.6 ± 0.28, 3.4 (0321) |
| 5850 | H | 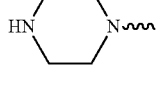 $C_5H_{12}N_2$ | RLIF | 40.5 ± 9.8 | 11.5 ± 0.14, 11.6 (0321) |
| 5566 | H | 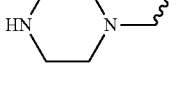 $C_6H_{14}N_2$ | RLNpfF | 18.2 ± 1.8 | 27.9 ± 2.97 |
| 541 | H | 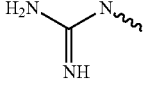 $C_2H_7N_3$ | RLNpfF | 6 ± 1.6 | 35.1 ± 4.10 |
| 5895 | H | 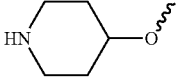 | X-RLIF (peptoid) | >>100 | >>180 |
| 5896 | OCH$_3$ |  | RLIF | 13.2 ± 3.7 | 12.3 ± 0.07 |
| 5919 | H | 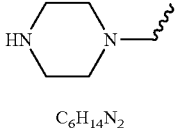 $C_6H_{14}N_2$ | RLIF | 16.69 | |
| 5923 | H | 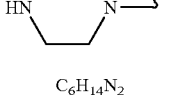 $C_6H_{14}N_2$ | ALIF | >100 (ALIF) | 149.18 |
| 5920 | OH | 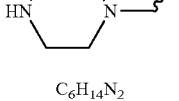 $C_6H_{14}N_2$ | RLIF | 5.86 | |
| 5922 | 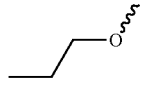 $C_4H_{10}O$ | 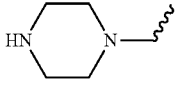 $C_6H_{14}N_2$ | RLIF | 4.8 | 42.19 |
| 5921 | H | $C_7H_{16}N_2$ | RLIF | 6.04, 6.6 | |
| 5965 | H | 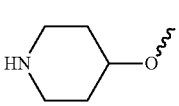 | Arg{βhomoLeu}NMePhe-NH$_2$ | 22.9 | 44.83 |

TABLE 10-continued (Table 10 discloses "RLIF" as SEQ ID NO: 52, "RLNpfF" as
SEQ ID NO: 54, "X-RLIF" as SEQ ID NO: 55 and "ALIF" as SEQ ID NO: 56)

| SCCP ID | R1 | R2 | Peptide link | IC50 (μm) CDK2/A2 | CDK4/D1 |
|---|---|---|---|---|---|
| 5966 | OH | piperazine ($C_6H_{14}N_2$) | Arg{βhomoLeu}NMePhe-$NH_2$ | 3.91 | 4.93 |
| 5968 | ethoxy ($C_3H_8O$) | piperazine ($C_6H_{14}N_2$) | Arg{βhomoLeu}NMePhe-$NH_2$ | 14.99 | 8.73 |
| 5967 | H | 1-methylpiperidin-4-yl-piperazine ($C_{12}H_{25}N_3$) | Arg{βhomoLeu}NMePhe-$NH_2$ | 10.03 | |
| 5969 | H | piperazinylmethyl ($C_7H_{16}N_2$) | Arg{βhomoLeu}NMePhe-$NH_2$ | 16.64 | 33.74 |
| 5970 | H | 2-methylpiperazinyl ($C_7H_{16}N_2$) | Arg{βhomoLeu}NMePhe-$NH_2$ | 4.91 | 297.37 |

As can be seen in Table 11, some of the Scaffold IV compounds show less activity as compared to unsubstituted picolinic acid, expect for the substitution of piperazine at the $R_2$ position.

TABLE 11

| SCCP ID | $R_1$ | $R_2$ | IC50 (μM) CDK2/A2 | CDK4/D1 |
|---|---|---|---|---|
| 525 | H | H | 39.3 ± 6.2/ 94.3 ± 14.9 (LIF) | 64 (LIF), 49 (LIF) (0321) |
| 5845 | $CH_3$ | H | >100 | 100~180 |
| 524 | MeO | H | 70.1 ± 7.9 | 100~180 |
| 523 | EtO | H | 47.5 ± 4.4/ 114 ± 10.5 (LIF) | 100~180 |
| 5856 | H | piperazinyl | ~100 | 34.2 |

The Scaffold V compounds of Table 12 based on hydroxyphenyl acetic acid show very good potency with two ethoxy substitutions on the 3 and 4 positions of the phenyl ring. Moreover, as substitution at the $R_1$ position gets bulkier, the potency of the Scaffold V compounds increase. While not wishing to be bound to any particular theory, the difference in potency between the 3-ethoxy and 3,4-diethoxy compounds may suggest that the 3,4-diethoxy compound binds to cyclin D in a distinct mode.

TABLE 12

| SCCP ID | $R_1$ | $R_2$ | IC50 (uM) CDK2/A2 | CDK4/D1 |
|---|---|---|---|---|
| 5854 | ethyl | H | >100 | >100 |
| 5853 | propyl | H | >100 | ~100 |
| 5855 | isobutyl | H | >>100 | 10~100 |

TABLE 12-continued

| | | | IC50 (uM) | |
|---|---|---|---|---|
| SCCP ID | $R_1$ | $R_2$ | CDK2/A2 | CDK4/D1 |
| 530 | | (ethoxy group) | 6.5 ± 1.3/ 15.5 ± 3.3 (LIF) | 24 (LIF) |

Arginine Isosteres

In one embodiment, isosteric arginine derivatives can be utilized as linkers between 35DCPT and a C-terminal dipeptide, βHomoLeu-NMethylPhe-NH$_2$. These synthetic amino acids can form amide bonds similarly to natural amino acids but have side chains that distinguish them.

Examples of arginine isosteres can include those having the following structure:

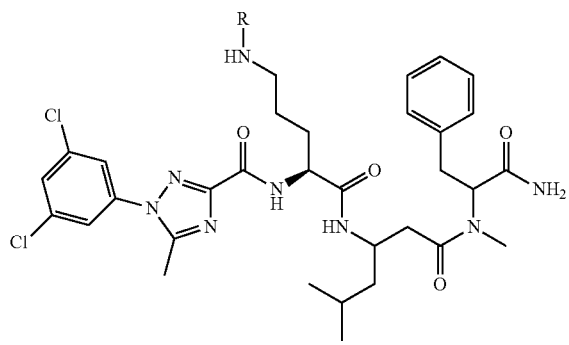

In which the R group can be one of the following:

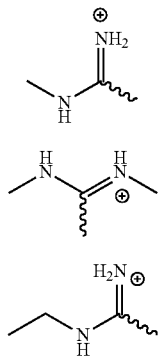

1

2

3

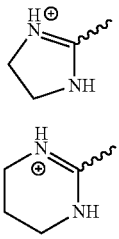

4

5

These synthetic amino acids can be synthesized and incorporated into the inhibitor compounds to enhance pharmacokinetics and inhibitory activities of peptides. The synthetic arginine derivatives obtained may (1) potentially mimic the interactions that are made between the CBM (ARG5) and the CBG (ASP283), (2) evaluate the steric requirements of this position, (3) improve drug-like properties, and (4) most likely improve the binding affinity of the compounds through favoring increased ion pairing interactions.

The replacement of Arg5 with various amino acids has been done with activity still present however at a decreased amount of 4-fold or greater. The arginine at this position is important for the binding affinity of HAKRRLIF (SEQ ID NO: 2) and therefore varying the functionality of these arginine derivative side chains can aid in the further development of the SAR and possibly the replacement for this position.

The arginine isosteres listed above were Fmoc-protected prior to solid phase peptide synthesis with a dipeptide C-cap, βHomoLeu-NMethylPhe-NH2. These compounds were then N-capped with 35DCPT. The alkylation of the guanidine group in these isosteres provided functionality and is believed to protect the guanidine groups from reacting during peptide synthesis. These side chains are expected to interact with ASP283 of the CBG and help establish further SAR.

These synthetic arginine derivatives have been utilized to replace Arg5 of the C-terminal pentapeptide (RRLIF). The side chains of these arginine derivatives can contain functional groups such as acyclic (methyl and ethyl) and cyclic (4,5-dihydro-1Himidazole and 1,4,5,6-tetrahydropyrimidine) groups. These groups may provide protection to the guanidine group to elude reactivity during peptide synthesis.

ADMET (absorption, distribution, metabolism, excretion, and toxicity) parameters were calculated for these arginine isosteres were calculated and are described in Table 13, below.

TABLE 13

| Isostere structure | Molecular Weight | Solubility Level | Absorption Level | LogP | # HBD | # HBA | # Rotatable Bonds | Polar Surface Area |
|---|---|---|---|---|---|---|---|---|
| Natural Arg 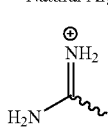 | 116.12 | 5 | 0 | 0.308 | 5 | 3 | 4 | 63.64 |

TABLE 13-continued

| Isostere structure | Molecular Weight | Solubility Level | Absorption Level | LogP | # HBD | # HBA | # Rotatable Bonds | Polar Surface Area |
|---|---|---|---|---|---|---|---|---|
| 1 | 130.13 | 5 | 0 | 0.514 | 4 | 3 | 5 | 49.65 |
| 2 | 144.15 | 4 | 0 | 0.720 | 3 | 3 | 5 | 38.03 |
| 3 | 142.15 | 5 | 0 | 0.863 | 4 | 3 | 6 | 49.65 |
| 4 | 142.13 | 4 | 0 | 0.538 | 3 | 3 | 4 | 38.03 |
| 5 | 156.15 | 4 | 0 | 0.601 | 3 | 3 | 4 | 38.03 |

As can be seen, alteration of the arginine affects mainly log P and PSA. The solubility and absorption levels remain consistent with the altered side chains and the number of HBD, HBA, and rotatable bonds are comparable across the table. However, the PSA values decrease by 13 to 25 units and the log P values increase with added functionality. With the increase in log P and the decrease in PSA, these arginine isosteres are expected to be promising replacements for natural arginine.

C-Terminal Partial Ligand Alternatives: Derivatives of 1-phenyl-1H-1,2,4-triazole-3 carboxamide.

The computational enrichment strategy described herein was applied to identify potential non-peptidic replacements for a C-terminal phenylalanine which has been verified as a critical determinant for binding to the cyclin groove. The general structure of the C capping groups was as follows:

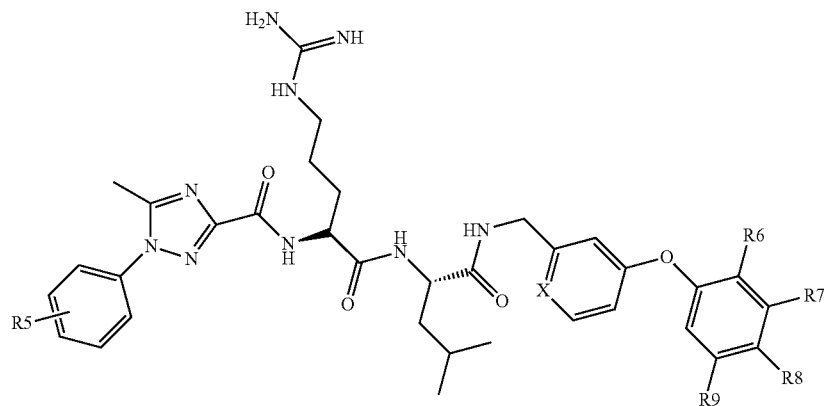

in which
$R_5$ is 4-chloro or 3,5-dichloro,
X is C, N
$R_6$, $R_7$, $R_8$, $R_9$ are independently H, $CH_3$, or halogen One method for forming the C-capping groups is as follows:

Resin is swelled in $CH_2Cl_2$ for 30 min. Fmoc-Leu-OH and DIPEA are added and the reaction allowed to stir for 2 hours. The solution is drained and the resin treated 3× with $CH_2Cl_2$/MeOH/DIPEA 17:2:1 to cap unreacted chloride. The resin is washed with $CH_2Cl_2$ 3× and DMF 3×. The resin is treated with 20% piperidine in DMF for 30 minutes. The solution is drained and the resin washed with $CH_2Cl_2$ 3× and DMF 3×. Fmoc-Arg(Pbf)-OH is dissolved in DMF along with HBTU and DIPEA. The solution is added to the resin and allowed to stir for 3 hours. The solution is drained and the resin is washed with $CH_2Cl_2$ 3× and DMF 3×. The resin is treated with 20% piperidine in DMF for 30 minutes. The solution is drained and the resin washed with CH$_2$Cl$_2$ 3× and DMF 3×. 1-(3,5-dichlorophenyl)-5-methyl-1H-1,2,4-triazole-3-carboxylic acid is dissolved in DMF along with HBTU and DIPEA. The solution is added to the resin and allowed to stir for 3 hours then sit overnight. The well is drained and washed with CH$_2$Cl$_2$ 3× and DMF 3×. The resin is cleaved with 5% TFA in CH$_2$Cl$_2$ and the crude is used as is after concentrating. The protected peptide 2-((S)-2-(1-(3,5-dichlorophenyl)-5-methyl-1H-1,2,4-triazole-3-carboxamido)-5-((E)-2-((2,2,4,6,7-pentamethyl-2,3-dihydrobenzofuran-5-yl)sulfonyl) guanidino) pentanamido)-4-methyl pentanoic acid is dissolved in methylene chloride and appropriate amine, (e.g. 3-phenoxybenzylamine etc), HBTU and triethylamine are added. The solution is stirred until HPLC indicates complete consumption of SM. The solution is concentrated and the residue partioned between EtOAc and water. The aqueous layer is back extracted with EtOAc and the combined organics are washed with 1N NaOH, 1N HCl, and brine. The organic is dried with NaSO$_4$, filtered and concentrated. Purification is performed by semiprep HPLC if necessary. The product is then treated with 95:2.5:2.5 TFA:H2O:TIPS and allowed to stir overnight. The solvent is removed and the residue triturated in ether. The solid is collected and purified by semiprep HPLC (Method: 0 to 80 over 20 min).

Specific C capping groups examined are described further in Table 14, below.

TABLE 14

| SCCP ID No. | R5 | X | R6 | R7 | R8 | R9 | CDK2/ cyclin A IC$_{50}$ (mM) | CDK4/ cyclin D1 IC$_{50}$ (mM) |
|---|---|---|---|---|---|---|---|---|
| 5807 | 4-chloro | C | H | H | H | H | 106.1 ± 26.2 | >200 |
| 5824 | 4-chloro | N | H | F | H | H | 53.2 ± 11.6 | >200 |
| 5823 | 4-chloro | N | H | H | F | H | 18.1 ± 4.0 | >200 |
| 5822 | 4-chloro | N | H | H | Cl | H | 54.4 ± 0.9 | >500 |
| 5825 | 4-chloro | N | CH$_3$ | H | H | H | 60 ± 3.5 | >500 |
| 5848 | 3,5-dichloro | N | H | Cl | H | H | 61 ± 10.8 | 120 |
| 5849 | 3,5-dichloro | C | H | Cl | H | Cl | >>180 | 120 |

An SAR study of the bis aryl ether compounds revealed that 3-phenoxybenzylamine was the most effective C-capping group although its activity relative to the native residue was diminished by approximately 2 fold (Table 8). It has been shown in various studies of CGI peptides that incorporation of a halogen into the aromatic ring of Phe derivatives results in substantial potency increase. Inclusion of 4-F Phe into the p21 CGI sequence resulted in a modest potency increase however 3-Cl Phe leads to a 10-20 fold enhancement in the CDK2/cyclin A context. Similar substitutions were incorporated into a 3-phenoxy(pyridin-2-yl)methylamine system as a close structural analogue of the phenoxybenzylamine core structure. These included the 2-methyl, 3 and 4-fluoro and 3 and 4-chloro substitutions of the phenoxy ring system.

Other C-caps have been identified and synthesized. In one embodiment a C-cap is 2-amino-N-ethyl-4-methyl-N-(3-phenylpropyl)pentanamide (C-cap in SCCP 6005 and 6014; Table 15, below).

Figure 7:
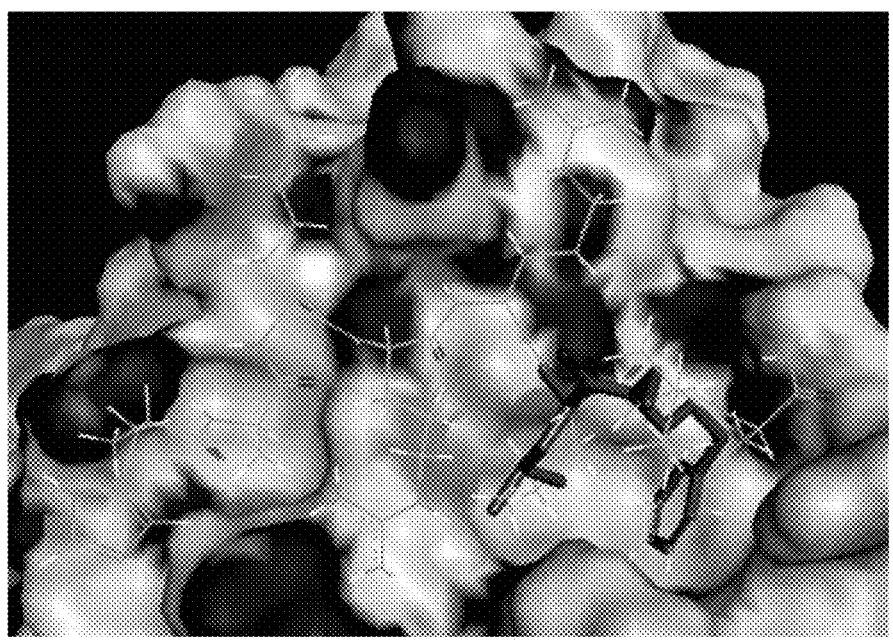
FIG. 7 illustrates one embodiment of a C-terminal capping group for inhibitors as described herein.

FIG. 7 illustrates this inhibitory group superimposed with HAKRRLIF (SEQ ID NO: 2) in the primary hydrophobic pocket of Cyclin A. From this image, it is evident that the phenyl propylamine group closely mimics the interactions of Phe8. The predicted binding mode of this group suggests that when incorporated as an inhibitor, this compound will aid in retaining the binding affinity of RRLIF in the primary hydrophobic pocket. The synthesis of this small molecule can be carried out via a two-step process with good versatility and can allow facile incorporation of an N-cap and arginine residues. This fragment, 2-amino-N-ethyl-4-methyl-N-(3-phenylpropyl)pentanamide, was synthesized via reductive amination followed by peptide synthesis as shown below and purified through semi-preparative High Performance Liquid Chromatography (prep-HPLC).

Ccap Coupling

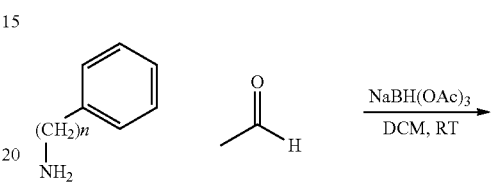

Peptide Synthesis

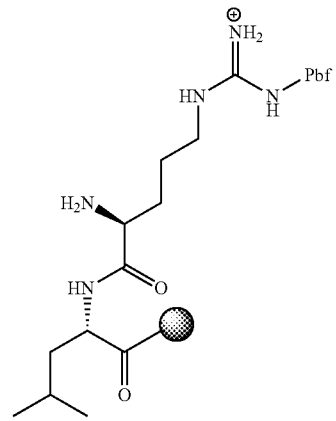

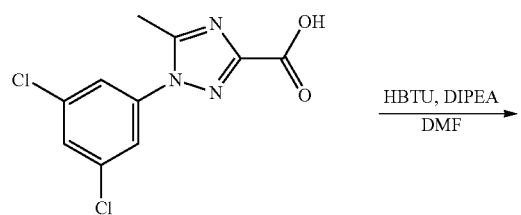

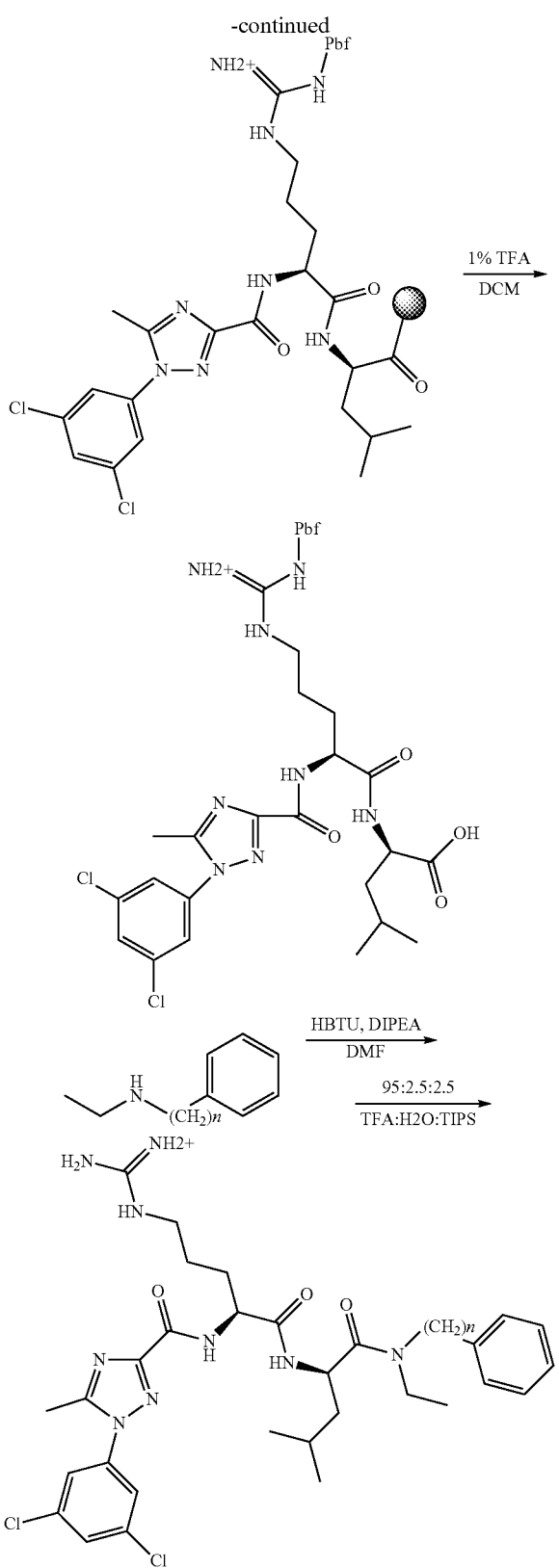

peptide in a solution phase coupling reaction. In the final step, the arginine side chain can be deprotected.

In addition to 2-amino-N-ethyl-4-methyl-N-(3-phenyl-propyl)pentanamide, other variations have also been synthesized as shown in Table 15, below. The general structure of each of these inhibitors is as follows:

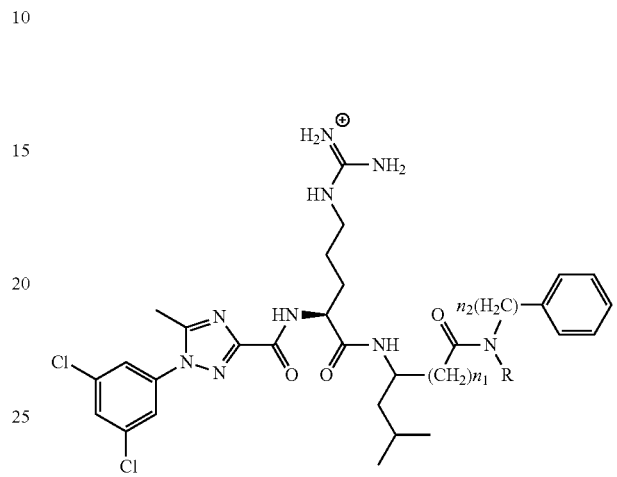

wherein
n1 is 1 or 0
n2 is 1, 2, or 3
the aromatic ring bonded to the $(CH_2)_{n2}$ group can include one or more halogens on the ring
R is hydrogen or ethyl.

TABLE 15

| SCCP | n1 | n2 | R | CDK2/Cyclin A $IC_{50}(\mu M)$ | CDK2/Cyclin D1 $IC_{50}(\mu M)$ |
|---|---|---|---|---|---|
| 6000 | 1 | 1 | H | >180 | >180 |
| 6001 | 1 | 1 | Et | >180 | >180 |
| 6002 | 1 | 2 | H | >180 | >180 |
| 6003 | 1 | 2 | Et | 85.62 | >180 |
| 6004 | 0 | 3 | H | 57.74 | >180 |
| 6005 | 0 | 3 | Et | >180 | >180 |
| 6014 | 0 | 3 | Et | 90.19 | >180 |

Each of the inhibitors of Table 15 have been coupled to 35DCPT-Arg and either Leu or Beta-Leu, the chemical structures of which are as follows:

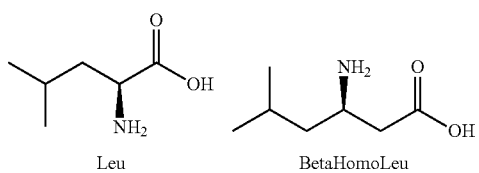

Leu   BetaHomoLeu

Initially in the formation scheme, the amine can undergo reductive amination to form a secondary amine. Second, the N-capped peptide can be made using solid phase synthesis. Next, the secondary amine can be coupled to the N-capped The 35DCPT N-cap has been determined to be the most potent in the replacement of the N-terminal. The variations in the table include different length alkyl chains, and a hydrogen or ethyl group at the R position. The natural leucine has been used in the synthesis of the analogs with a propyl alkyl chain (SCCP 6004 and 6005). Natural leucine has the amine group on the carbon in the a position, to the carboxylic acid, which helps orient these C-caps in a binding mode similarly to the native ligand, aids in the positioning of these fragments in the primary hydrophobic pocket, and potentially aids in retaining the binding affinity of LIF. The non-natural βHomo-leucine was used in the synthesis of the analogs with either methylene or ethylene alkyl chains (SCCP 6000, 6001, 6002, and 6003). Beta amino acids contain an additional methylene group between the carboxylic acid and the amine group where the extra carbon theoretically should adjust for the shorter alkyl chains and help position the fragments in the primary hydrophobic pocket to closely mimic the native ligand. Following peptide synthesis (of N-cap-Arg-Leu/βLeu), coupling with the C-cap and arginine deprotection, these compounds were purified through prep-HPLC.

The compounds were found to be 88-98 percent pure, by UV, and the MS results confirmed the identity of the desired compound. Once the compounds were characterized, their binding affinities were tested by FP assay. The competitive binding assay determined that the ethyl phenylethan-amine C-cap coupled to 35DCPT-R-βHomoL (SCCP 6003) has an IC50 value of 85.62 µM and the phenylpropylamine and ethyl phenylpropyl amine C-caps, coupled with 35DCPT-RL (SCCP 6004 and 6014 respectively), had an IC50 values of 57.74 µM, and 90.19 µM against CDK2/cyclin A, respectively. All other compounds in the table have IC50 values greater than 180 µM against CDK2/cyclin A.

Table 16, below, presents additional embodiments of inhibitors as have been developed by use of the methods described herein. Prostate (DU145) and osteosarcoma (U2OS) cell lines were treated with SCCP 5963 and 5964, with results presented in Table 16. These particular inhibitors have the general structure of:

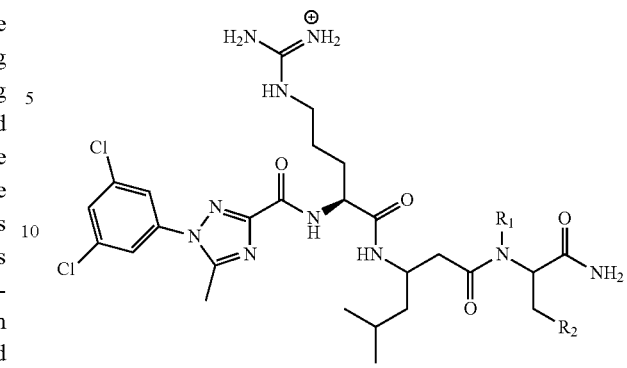

TABLE 16

| | | | Competitive Binding Assay | | Cell Proliferation Assay | |
| --- | --- | --- | --- | --- | --- | --- |
| | | | CDK2/ Cyclin A | CDK4/ Cyclin D1 | DU 145 | U2OS |
| SCCP | R1 | R2 | IC50 (µM) | IC50 (µM) | IC50 (µM) | IC50 (µM) |
| 5963 | Me | phenyl | 6.49 ± 0.27 | >100 | 36.5 ± 2.6 | 30.7 ± 2.7 |
| 5964 | H | thiophene | 7.91 ± 5.08 | >100 | 21.8 ± 0.32 | 18.3 ± 1.5 |

ADMET (absorption, distribution, metabolism, excretion, and toxicity) parameters were calculated for SCCP 5963, 5964, and 6004 and are described in Table 17. ADMET parameters such as solubility between 0-1 and absorption between 3-4, Lipinski's Rule of 5 which states that the molecular weight (MW) for oral bioavailable drugs should be <500, log P<5, the number of hydrogen bond donors (HBD)<5, and the number of hydrogen bond acceptors (HBA)<10 and the number of rotatable bonds (≤10) and polar surface area (PSA) (≤140) are ideal for cell permeability. SCCP 5964 was the most active in the cell proliferation assay and when compared to SCCP 5963, it was found to have a more ideal solubility level, lowest log P value, fewer HBA and rotatable bonds but has the highest PSA. The most active compound from the C-caps was SCCP 6004. This compound has comparable solubility and absorption levels and has fewer HBD, HBA, and rotatable bonds. The log P value for SCCP 6004 was significantly higher than that of SCCP 5964 but has almost 1.5 fold less PSA. This may conclude that SCCP 6004 can have similar cell permeability and activity as SCCP 5964. With these ADMET values it can be predicted that SCCP 6004 can have greater cell permeability but may have slightly less activity based on its binding affinity in the FP assay.

TABLE 17

| SCCP | Molecular Weight | Solubility Level | Absorption Level | LogP | # HBD | # HBA | # Rotatable Bonds | Polar Surface Area |
|---|---|---|---|---|---|---|---|---|
| 5963 | 714.292 | 2 | 3 | 3.163 | 8 | 14 | 18 | 214.21 |
| 5964 | 706.233 | 1 | 3 | 2.255 | 9 | 14 | 18 | 251.25 |
| 6004 | 658.279 | 2 | 3 | 4.044 | 8 | 12 | 17 | 181.65 |

Table 18, below, presents another series of C-caps as may be incorporated in an inhibitor. These C-caps can be synthesized according to a scheme as provided above for the materials of Table 15. The C-caps of Table 18 differ from SCCP 6000-6005 and 6014 by the group in the Leu6 position which is either leucine or βHomo-leucine. These C-caps can contain phenylalanine, histidine, βHomophenylalanine, or βHomo-histidine depending on the length of the alkyl chain at the n2 position. These derivatives can help further establish the SAR for the Leu6 position. The variation of the ring size plus the addition of potential ion-pairing interaction of the imidazole ring of histidine can aid in the determination of which functional group should be present to retain or enhance the binding affinity of the Leu6 position. Leu6 has previously been determined to be the most critical amino acid of the octamer (HAKRRLIF (SEQ ID NO: 2)) and therefore its replacement can be challenging but has also been shown that this position is capable to be replaced with a small molecule. The inhibitors of Table 18 have the structure:

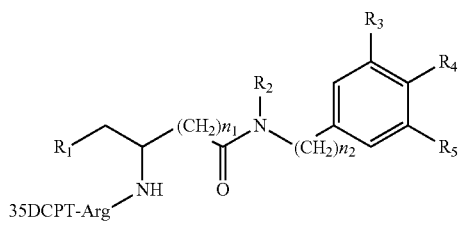

wherein
n1 is 0 or 1,
n2 is 3,
R1 is an arginine side chain,
R2 has one of the following structures:
R2 has one of the following structures:

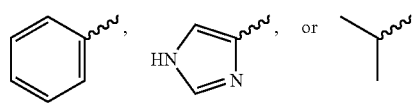

R3, R4, and R5 are independently hydrogen or a halogen.

TABLE 18

| Sample no. | n1 | n2 | R2 | R3 | R4 | R5 |
|---|---|---|---|---|---|---|
| 1 | 0 | 3 | phenyl | H | H | F |
| 2 | 1 | 3 | phenyl | H | H | F |
| 3 | 0 | 3 | imidazole | H | H | F |
| 4 | 1 | 3 | imidazole | H | H | F |
| 5 | 0 | 3 | isopropyl | Cl | H | Cl |
| 6 | 0 | 3 | isopropyl | H | Cl | H |
| 7 | 0 | 3 | isopropyl | F | H | F |
| 8 | 0 | 3 | isopropyl | H | F | H |

Table 19, below, presents the ADMET parameters for these compounds.

TABLE 19

| Sample no. | Molecular Weight | Solubility Level | Absorption Level | LogP | # HBD | # HBA | # Rotatable Bonds | Polar Surface Area |
|---|---|---|---|---|---|---|---|---|
| 1 | 706.279 | 2 | 3 | 4.510 | 8 | 12 | 18 | 181.65 |
| 2 | 692.263 | 2 | 3 | 4.054 | 8 | 12 | 17 | 181.65 |
| 3 | 682.254 | 2 | 3 | 2.398 | 9 | 14 | 17 | 210.33 |
| 4 | 696.64 | 2 | 3 | 2.083 | 9 | 14 | 17 | 210.33 |
| 5 | 726.201 | 1 | 3 | 5.373 | 8 | 12 | 17 | 181.65 |
| 6 | 692.240 | 1 | 3 | 4.708 | 8 | 12 | 17 | 181.65 |
| 7 | 694.260 | 1 | 3 | 4.455 | 8 | 12 | 17 | 181.65 |
| 8 | 676.269 | 2 | 3 | 4.250 | 8 | 12 | 17 | 181.65 |

These compounds have comparable solubility and absorption levels. Compound No. 4 has lower log P and PSA values than SCCP 5964, which may indicate increased cell permeability and activity. Compound No. 3 has a comparable log P value but a lower PSA value which may result in this compound having comparable permeability and activity as SCCP 5964. All other compounds have greater log P values, similar number of HBD, HBA and rotatable bonds, and lower PSA values. This may contend that these compounds may have cell permeability and activity but will most likely not be greater than that of SCCP 5964.

Following development of C-terminal and N-terminal groups, certain optimized terminal groups can be combined into individual molecules. While the unsubstituted bis-aryl ether (incorporating 3-phenoxybenzylamine) had decreased activity when combined with the 3,5-DCPT-Arg-Leu N-terminal group relative to the previous peptide context (Arg-Arg-Leu-3PBA), addition of halogen substituents onto the aromatic ring contacting the primary lipophilic site resulted in recovery of binding and comparable activity to the native peptide sequence. Individually, a 3-fluoro and 4-fluoro substituted bis-aryl ether had enhanced potency compared to the unsubstituted. Addition of these halogens follows a similar pattern to that observed in the peptide context where incorporation of either a 3 or 4 substituted phenylalanine residue resulted in significant potency gains. These results illustrate that removal of peptide determinants and substitution with fragment like compounds can change the binding mode of an inhibitor and result in potency loss. The data obtained also suggests that reoptimization through SAR studies can regain potency lost in this way and that more drug-like and less peptidic inhibitors can be obtained.

Examples of such molecules include the following cyclin A selective compounds:

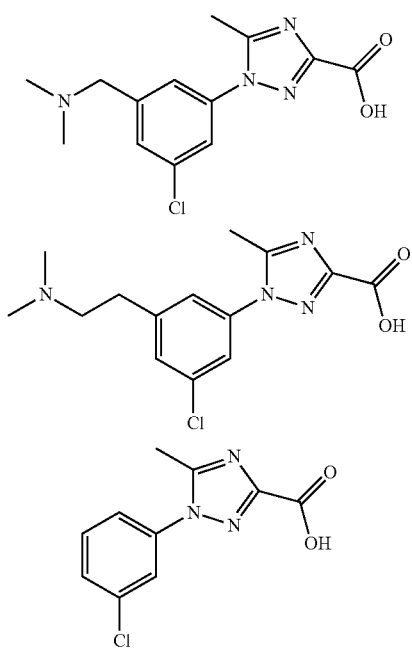

and the following cyclin D selective compounds:

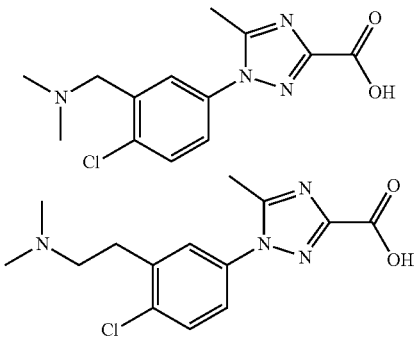

-continued

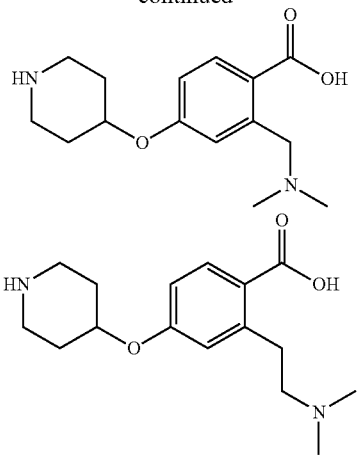

Figure 6:
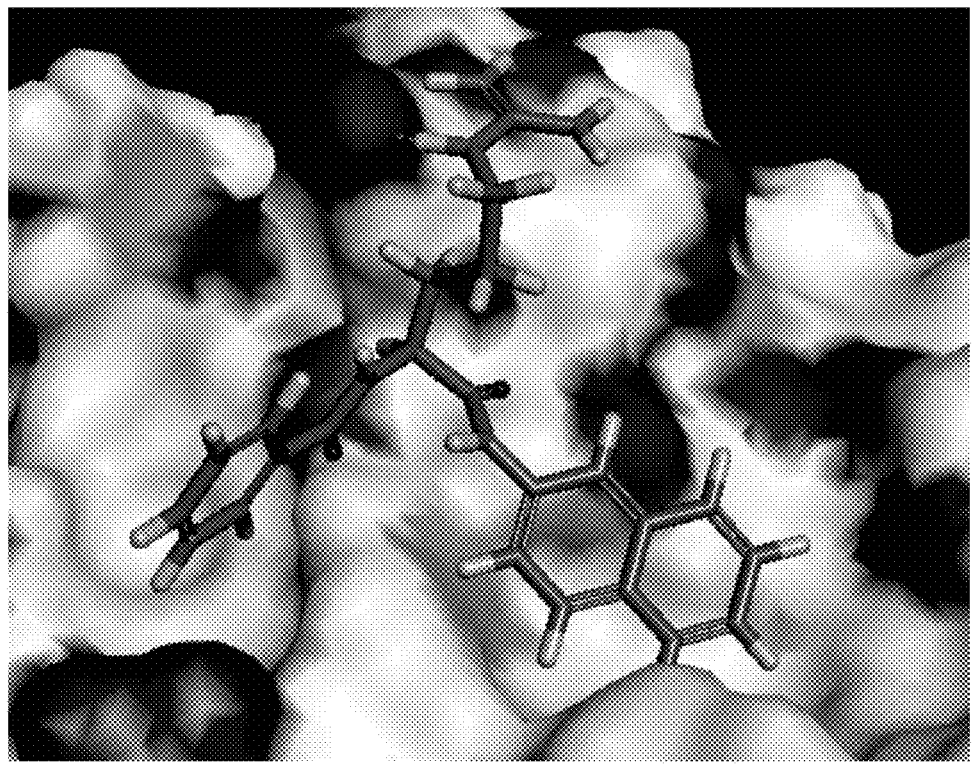
FIG. 6 illustrates an inhibitor, N-(5-guanidino-1-(naphthalen-2-ylamino)-1-oxopentan-2-yl)benzamide, designed according to disclosed methods.

In one embodiment, picolinamide and benzamide N-cap scaffolds can be used for potential small molecules to replace HAKRRLIF (SEQ ID NO: 2) or to aid in the design of novel C-caps. The validated optimized parameters can be used in the docking of the resulting compounds. One inhibitor developed from this approach is N-(5-guanidino-1-(naphthalen-2-ylamino)-1-oxopentan-2-yl)benzamide (FIG. 6), which contains a benzamide N-cap, a naphthalene C-cap, and an arginine in the Arg5 position.

The benzamide Ncap, of this small molecule, nicely forms an H-bond with Trp217 and the arginine ion-pairs well with Asp283 and H-bonds with Glu254. In addition, the naphthalene Ccap has good complementarity with the primary hydrophobic pocket. This compound also ranks well in the overall scoring functions. LigScore2_Dreiding, -PLP1, and -PLP2 have been determined to be good scoring functions for the prediction of potent small molecules. This compound is ranked within the top twenty five percent of all ligands docked with scores of 5, 56.06, and 55.88 for LigScore2_Dreiding, -PLP1, and -PLP2, respectively. With the observed intermolecular interaction and the resulting scoring functions, this molecule was expected to have activity against both Cyclin A and D1. However, upon testing in the FP assay this fragment was found to be weakly binding.

Modeling the Interactions of p27 with Cyclin D1 Structures

CDK4/cyclin D1 have been shown to associate with p27 and that this interaction promotes the formation of the complex. It is also known that different states of the ternary complex exist, where p27 may bind to generate inhibited and non-inhibited CDK4 species. A critical aspect of this process is the phosphorylation of p27 on Y88, sited on the $3_{10}$ helix which inserts into the ATP binding site of CDK4 in the inhibited complex. Phosphorylation presumably leads to dissociation of the helix from the ATP cleft through disruption of hinge H-bonding interactions and through repulsion of the phosphate with nearby acidic residues. In this non-inhibited form, p27 however, must still maintain affinity for the complex in order to sequester the inhibitor from CDK2/cyclin E complexes and allow cell cycle progression. A major contribution to this binding is through cyclin D1/p27 interactions and assisted by the CBM and other residues. So as to construct a model structure of p27/cyclin D1 interactions, cyclin D1 isolated from the 2W96 crystal structure was overlayed with the CDK2/cyclin A/p27 ternary complex (1JSU). After deletion of the CDK2, cyclin A and non cyclin D1 interacting p27 residues, the newly formed complex was subjected to energy minimization. After convergence of the structure to a suitable minimum, and examination of the resulting interactions, a plausible structural basis for the interactions of p27 with cyclin D1 interactions was described. Subsequent to generation of this structure, the interaction energies of individual p27 residues with cyclin D1 were generated and compared with those for cyclin A. Significant differences in the intermolecular interactions are apparent for several residues, several of which are noted in the octapeptide complexes described in the above sections. These include, A28, N31, F33, V36, L41 and L45. Comparison of the molecular surface for the p27 interacting residues of cyclin A vs. those of cyclin D1 indicated that profound differences exist specifically in the region where the C-terminus of the inhibitory protein exits from the primary hydrophobic pocket. The more extensive cleft of cyclin D1, led to the hypothesis that incorporation of a suitable residue C-terminal to the glycine would lead to preferential binding vs. cyclin A. Computational design of a number of different residues suggested that methionine would be a good candidate for more optimal interactions and therefore synthesis and testing of the p27 sequences shown in Table 5, was completed and confirmed this conclusion.

Figure 5:
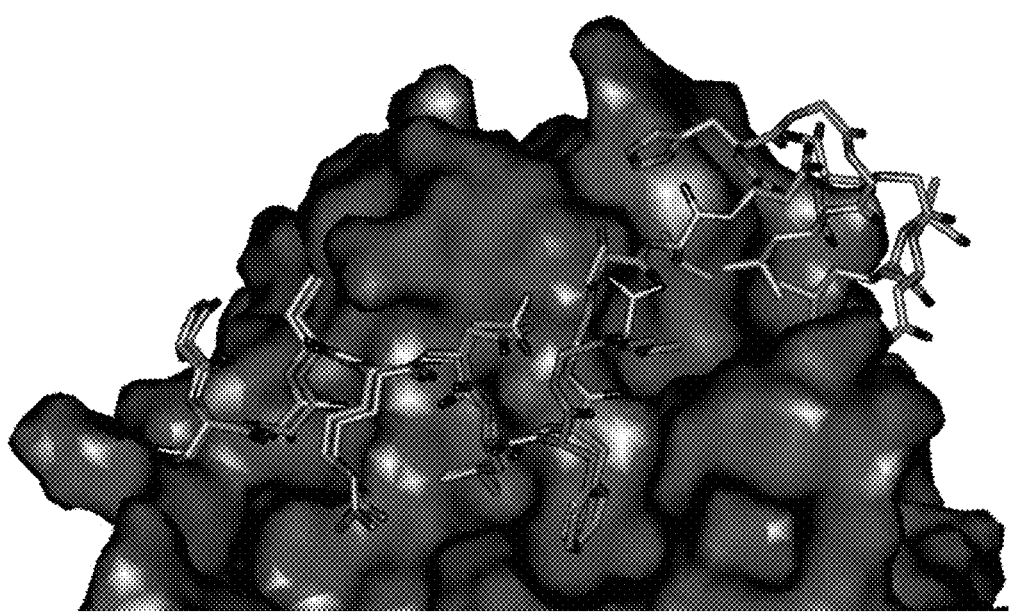
FIG. 5 illustrates a modeled complex of the p27 residues 25-49 with cyclin D1 (2W96) overlaid with SAKRNLFGM (SEQ ID NO: 1).

FIG. 5 illustrates a modeled complex of p27 residues 25-49 with Cyclin D1 (2W96) overlayed with SAKRN-LFGM (SEQ ID NO: 1). The P35 and V36 interacting site on cyclin D1 is the region shown to provide a more extensive hydrophobic pocket than in the cyclin A2 context and which was exploited by methionine substitution. As may be seen in FIG. 5, the P35 and V36 contacting site of cyclin D1 has a larger accessible volume and therefore has suboptimal interactions with p27. This was confirmed in the per residue interaction energy calculation which yielded values of −1.9 and -3.6 kcal/mol for D1 and A respectively. The lack of increase of the Asparagine containing sequence may be explained by the formation of an intramolecular H-bond observed in the crystal structure and which precludes optimal interactions of the methionine. Substitution of this residue with an alanine resulted in a 2 fold potency enhancement as predicted. As illustrated (FIG. 5), the linear side chain of the P35M analog extends with a high degree of complementarity into the extension of the primary hydrophobic pocket. These results suggest that this extended binding site in cyclin D1 could be exploited in the design of small molecule cyclin groove inhibitors.

LEU-PHE Mimetics

Based on commercially available compounds with appropriate functionality to mimic both Leu6 and Phe8 and by use of the disclosed methods, additional compounds for use as C-caps as described below in Table 20 were designed, synthesized and coupled to 35DCPT-Arg5. These compounds can have the general structure:

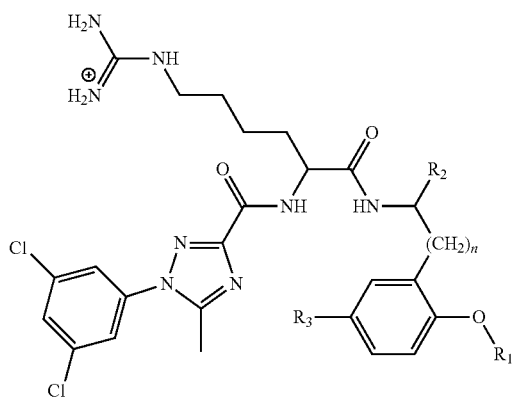

wherein
n is 0 or 1
R1, R2, and R3 are independently hydrogen, isobutyl, methyl, ethyl, or propyl groups.

These Leu-Phe mimetics contain either isobutyl or isopropyl groups at the R2 position to help retain the interactions of Leu6 in the primary hydrophobic pocket shown to be the most important residue of the CBM. Also, there are varying alkyl groups at the R1 position to mimic Phe8 in the pocket. The general structure of the C-caps of Table 20 is as follows:

TABLE 20

| SCCP | n | R1 | R2 | R3 | CDK2/Cyclin A IC$_{50}$ (μM) | CDK2/Cyclin A IC0$_{50}$ (μM) |
|---|---|---|---|---|---|---|
| 5977 | 0 | iBut | iBut | H | 148.4 | >180 |
| 5978 | 0 | iBut | iBut | H | >180 | >180 |
| 5979 | 0 | Pr | iBut | H | 181.2 | >180 |
| 5980 | 0 | Pr | iBut | Me | >180 | >180 |
| 5981 | 1 | Me | iBut | H | >180 | >180 |
| 5982 | 1 | Me | iBut | H | >180 | >180 |
| 5983 | 0 | Et | iBut | H | 164.02 | >180 |
| 5984 | 0 | Et | iBut | H | >180 | >180 |
| 5985 | 0 | Me | iBut | H | >180 | >180 |

Following solid phase synthesis and coupling with the C-cap, the Leu-Phe mimetics were purified via prep-HPLC. As these compounds have a chiral center and were purchased as a racemic mixture, diastereomers were formed during synthesis. However, not all of the isomers were able to be successfully separated by prep-HPLC but the isomers that were separated the isomers that eluted first were those with activity. The isomers with activity would be the R isomer, as the S isomer would not be expected to have activity against the CDK/cyclin complexes because only S amino acids have been shown to be active. The compounds were 79-98 percent pure, by UV and the MS results the identity of desired compounds were confirmed. Subsequent to full characterization of the compounds their binding affinities were tested via FP assay.

Figure 8:
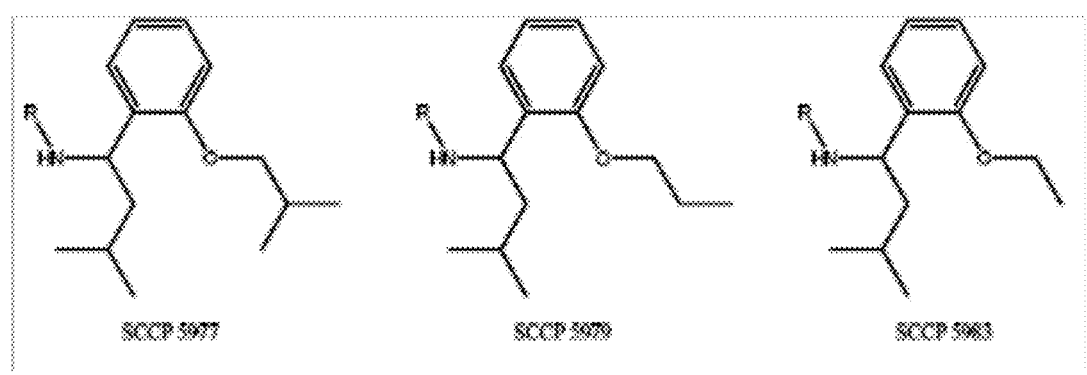
FIG. 8 illustrates three inhibitors designed according to disclosed methods.

Of the compounds listed in Table 20, only SCCP 5977, 5979 and 5983 showed activity against CDK2/cyclin A (FIG. 8) while none displayed significant binding to CDK4/cyclin D1. SCCP 5977 showed an IC50 value of 148.4 μM, SCCP 5979 had an IC50 value of 181.2 μM, and SCCP 5983 had an IC50 value of 164.02 μM all against CDK2/cyclin A. These compounds were not active against CDK4/cyclin D1. The R group for each of these compounds was 35DCPT-Arg.

The isobutyl group mimicking Leu6, in all the compounds, retained some of the binding affinity and the various alkoxy groups mimicking Phe8 had a significant effect on the activity of each compound on CDK2/cyclin A. SCCP 5977 contains an isobutyl group to mimic the Phe8 position in the primary pocket. This compound had an IC50 value of 148.4 μM against CDK2/cyclin A. SCCP 5979 has a propyl group reaching in to the pocket in replacement of Phe8 and has an IC50 value of 181.2 μM against CDK2/cyclin A. Lastly, SCCP 5983 contains an ethyl group which showed to be slightly less potent against CDK2/cyclin A with an IC50 value of 164.02 μM. All other compounds (SCCP 5978, 5980-5982, 5984, and 5985) were not active against either CDK2/cyclin A or CDK4/cyclin D1.

The isobutyl group replacement for Phe8 (SCCP 5977) appeared to be a good alkyl group compared to the propyl group (SCCP5979) and the ethyl group (SCCP 5983). The additional methyl group of the isobutyl seemed to be a contributor to the retention of potency compared to the propyl group. SCCP 5977 showed an IC50 value of 148.4 µM, SCCP 5979 with 181.2 µM and SCCP 5983 with 164.02 µM. The isobutyl side chain (SCCP 5977) proved to be most potent against CDK2/cyclin A with an IC50 value of 148.4 µM.

In summation, comparison of the cyclin binding grooves of cyclin D1 structures obtained recently through crystallographic studies provides considerable insight into the structural requirements for cyclin A2 vs. D1 selectivity and for differential binding of CGI peptide analogues. While the binding of peptide inhibitors of cyclin A and E substrate recruitment has been extensively characterized, little information has been made available describing the determinants of cyclin D inhibition. Structural analysis revealed that two key amino acid substitutions in the cyclin D1 groove have a major impact on peptide inhibitor binding. Exchange of one of the two acidic residues interacting with Arg4 (Asp216 and Glu220), with Thr62 significantly decreases the calculated enthalpic contribution to binding and is suggestive of a large decrease in affinity. In order to determine if the predicted decrease in the electrostatic interaction energy is significant in contributing to cyclin A selectivity, the arginine isostere citrullene was incorporated into the p21 8mer, HAKCitRLIF (Table 5) (SEQ ID NO: 26). It was predicted that due to the less acidic environment of the Arg contacting residues in cyclin D, that the potency decrease would be less marked in this context. In reality however, a similar drop off was demonstrated in both scenarios and thus indicating otherwise. Closer examination of the peptide-cyclin D1 structure suggests that the urea carbonyl of citrullene is within H-bonding distance of the OH group of Thr62. This interaction would therefore compensate for the decreased capacity to ion pair and result in a similar potency decrease.

As described, the second major difference between the two cyclins is in the exchange of Leu214 in cyclin A for Val60 in cyclin D. The smaller Valine sidechain projects down toward the base of this hydrophobic pocket with the net effect that the y methyls are brought into closer proximity to the peptide inhibitor side chains which insert into this pocket. This substitution therefore decreases the volume of the primary hydrophobic pocket in the latter and thereby results in lower affinity of CGI peptides containing phenylalanine. Cyclin bound complexes were generated for a series of peptides previously determined to have varying affinities for cyclin A and cyclin D1 and possessing different C-terminal sequences. The calculated binding energies for these complexes correlated well not only for IC50s determined for cyclin A and D1 individually but also for the selectivity of the peptides observed. These results therefore determined that in addition to the X-ray structures used, the model structures for the peptide-cyclin complexes gave valid results and that this information is useful in the potential design and optimization of improved cyclin D1 inhibitors. From these observations, the hypothesis was proposed that due to the decreased volume of the primary hydrophobic pocket relative to cyclin A, that the incorporation of non-natural amino acids with differing cyclic sidechains than phenylalanine might be tolerated to a greater degree. To this end, the results presented confirm that this is indeed the case however these are dependent on the peptide context. As has been previously structurally characterized, the presence of a spacer residue between the critical Leu and Phe functions to allow a geometrical arrangement of the two side chains that interacts with a greater degree of complementarity and therefore increases binding affinity relative to peptides with no spacer. The results suggest that non-spacer containing peptide, SAKRRLXG (SEQ ID NO: 3), has a binding mode which is more conducive and tolerant of smaller cyclic sidechains. In order to probe this further, a 3D structure for each of the synthesized analogs in complex with both cyclins was generated and further to this, their non-bonded interaction energy calculated. These results suggested that a correlation between the observed potencies and the calculated affinity existed and confirmed that for both 5 membered rings, a decrease in binding of these analogues would be expected. The structural basis for the greater affinity of the furylalanine (X1) vs. the 2-thienylalanine (X2) in the p107 context is apparent from the modeled structure. The closer proximity of the heteroatom to Val60 in the peptide without the spacer residue results in displacement of the larger sulfur containing Phe replacement (thiophene ring) and lower relative affinity. In the p21 peptide, the conformational preference allowed by the spacer residue, results in the heteroatom pointing to the back wall of the primary hydrophobic pocket, away from Val60. As the heteroatom projects into more expansive region, the larger sulfur atom provides greater complementarity with K96 and Q100 resulting in increased affinity in the thienylalanine derivative. Changing the context of the heterocyclic sulfur atom as in X3 resulted in potency increase of SAKRRLX3G (SEQ ID NO: 11) for cyclin A but an increase in cyclin D1 affinity. The larger hydrophobic pocket in cyclin A may accommodate the bulky sulfur atom more readily than may the cyclin D1 site decreased in volume by Val60. Examination of the intermolecular contacts for the cyclohexylalanine derivative X6, a bulkier Phe replacement as a result of the unsaturated ring, again provided insight into the differing potencies for peptides containing this residue with cyclin D1. Modeling of the complex of SAKRRLX6G (SEQ ID NO: 14) with cyclin D1 (12 fold decrease in IC50), suggested that in order to maintain productive binding, the CHA sidechain is brought in close proximity to Val60 resulting in unfavorable contacts. For the HAKRRLIX6 (SEQ ID NO: 22) inhibitor (4 fold loss in potency), the sidechain may adopt a more favorable position, contacting several residues of the primary binding site in line with its higher relative potency. The dramatic decreases in inhibition of the pyridylalanine derivatives X7 and X8 relative to the native phenylalanine cannot readily explained in terms of different interactions with the cyclin groove. A probable scenario is that the pyridyl ring is solvated to a greater degree relative to the phenyl and therefore a desolvation penalty would disfavor binding. A number of substitutions in the cyclin groove recognition motif have been incorporated in the N-terminal and arginine binding site and provide additional information on the tolerance of sequence changes upon binding to the secondary hydrophobic and acidic regions of cyclin D1.

Disclosed methods can provide a plurality of benefits as compared to conventional approaches that are used for fragment based design in drug development. Firstly as potential fragment alternatives are evaluated while ligated to truncated peptide sequences, a successful hit in the disclosed methods provides a fragment ligated inhibitor that recapitulates binding of the intact native peptide. The truncated peptide therefore acts as an affinity scaffold and obviates the need for a highly sensitive detection method. This stands in contrast to conventional fragment based design that typically requires methods for detecting milimolar binding affinity. Another requirement of fragment based design utilizing crystallography as a detection method is the necessity for highly soluble fragments since by definition they must have much higher solubility than their binding constant. The present methods can evaluate fragments while ligated to a peptide and therefore can provide solubility through the polarity of the peptide sequence. Furthermore optimization of PLAs can be performed while in the fragment ligated inhibitor context of the disclosed method therefore again avoiding requirement for expensive and difficult methods for binding determination.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A synthetic CDK/cyclin inhibitor that inhibits interaction of a complex formed between a first CDK protein and a first cyclin protein with a substrate of the complex, the synthetic CDK/cyclin inhibitor comprising a peptide sequence and a capping group bonded to the N-terminus of the peptide sequence, the capping group comprising a substituted benzoic acid, the peptide sequence comprising Arg-βhomoLeu-3-thienylalanine, the capping group having the following structure:

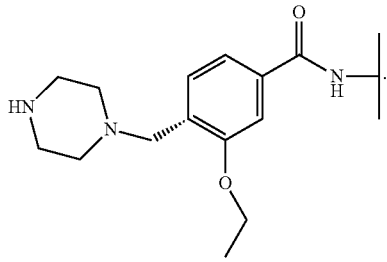

2. The synthetic CDK/cyclin inhibitor of claim 1, further comprising a capping group bonded to the C-terminus of the peptide sequence.

3. The synthetic CDK/cyclin inhibitor of claim 2, wherein the capping group bonded to the C-terminus is 2-amino-N-ethyl-4-methyl-N-(3-phenylpropyl)pentanam ide.

4. The synthetic CDK/cyclin inhibitor of claim 2, wherein the capping group bonded to the C-terminus is an ethyl phenylethan-amine, a phenylpropylamine, or an ethyl phenylpropyl amine.

5. The synthetic CDK/cyclin inhibitor of claim 2, wherein the capping group bonded to the C-terminus includes phenylalanine, histidine, βHomophenylalanine, or βHomo-histidine.

* * * * *

```
                          SEQUENCE LISTING

<160> NUMBER OF SEQ ID NOS: 66

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ala Lys Arg Asn Leu Phe Gly Met
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Ala Lys Arg Arg Leu Ile Phe
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid

<400> SEQUENCE: 3

Ser Ala Lys Arg Arg Leu Xaa Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid

<400> SEQUENCE: 4

His Ala Lys Arg Arg Leu Ile Xaa
1               5

<210> SEQ ID NO 5
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 5

Arg Arg Leu Ile Phe
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ala Lys Arg Arg Leu Phe Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Val Lys Arg Arg Leu Asp Leu
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cit

<400> SEQUENCE: 8

Xaa Arg Leu Ile Phe
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 2-furylalanine

<400> SEQUENCE: 9

Ser Ala Lys Arg Arg Leu Ala Gly
1               5

<210> SEQ ID NO 10
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 2-thienyl alanine

<400> SEQUENCE: 10

Ser Ala Lys Arg Arg Leu Ala Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 3-thienyl alanine

<400> SEQUENCE: 11

Ser Ala Lys Arg Arg Leu Ala Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Cyclobutylalanine

<400> SEQUENCE: 12

Ser Ala Lys Arg Arg Leu Ala Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Cyclopentylalanine

<400> SEQUENCE: 13

Ser Ala Lys Arg Arg Leu Ala Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Cyclohexylalanine
```

```
<400> SEQUENCE: 14

Ser Ala Lys Arg Arg Leu Ala Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 3-pyridylalanine

<400> SEQUENCE: 15

Ser Ala Lys Arg Arg Leu Ala Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 4-pyridylalanine

<400> SEQUENCE: 16

Ser Ala Lys Arg Arg Leu Ala Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 2-furylalanine

<400> SEQUENCE: 17

His Ala Lys Arg Arg Leu Ile Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 2-thienyl alanine

<400> SEQUENCE: 18

His Ala Lys Arg Arg Leu Ile Ala
1               5

<210> SEQ ID NO 19
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-thienyl alanine

<400> SEQUENCE: 19

His Ala Lys Arg Arg Leu Ile Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Cyclobutylalanine

<400> SEQUENCE: 20

His Ala Lys Arg Arg Leu Ile Ala
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Cyclopentylalanine

<400> SEQUENCE: 21

His Ala Lys Arg Arg Leu Ile Ala
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Cyclohexylalanine

<400> SEQUENCE: 22

His Ala Lys Arg Arg Leu Ile Ala
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (8)..(8)
<223> OTHER INFORMATION: 3-pyridylalanine

<400> SEQUENCE: 23

His Ala Lys Arg Arg Leu Ile Ala
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 4-pyridylalanine

<400> SEQUENCE: 24

His Ala Lys Arg Arg Leu Ile Ala
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4FPhe

<400> SEQUENCE: 25

Arg Arg Leu Ile Phe
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Cit

<400> SEQUENCE: 26

His Ala Lys Xaa Arg Leu Ile Phe
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cit

<400> SEQUENCE: 27

Arg Xaa Leu Ile Phe
```

```
<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Ala Lys Thr Arg Leu Ile Phe
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ala Lys Arg Asn Leu Phe Gly
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ala Lys Arg Ala Leu Phe Gly Met
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Ala Lys Arg Arg Leu Phe Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Val Lys Arg Arg Leu Phe Gly
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (7)..(7)
<223> OTHER INFORMATION: 3-chlorophenylalanine

<400> SEQUENCE: 33

Pro Val Lys Arg Arg Leu Phe Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4FPhe

<400> SEQUENCE: 34

Arg Arg Leu Asn Phe
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Pro Leu Ile Phe
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ala Leu Ile Phe
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Arg Leu Phe Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 38

Arg Gly Leu Ile Phe
1               5

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Arg Leu Phe
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Beta-homoLeu

<400> SEQUENCE: 40

Arg Arg Leu Phe
1

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Beta-homoLeu

<400> SEQUENCE: 41

Arg Arg Leu Phe Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any DMAM modified residue

<400> SEQUENCE: 42

Arg Xaa Leu Ile Phe
1               5

<210> SEQ ID NO 43
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DMAM-Ala residue

<400> SEQUENCE: 43

Arg Ala Leu Ile Phe
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 44

Ser Ala Lys Arg Arg Leu Phe Gly
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term OH

<400> SEQUENCE: 45

Ser Ala Lys Arg Arg Leu Phe Gly
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 3-thienyl alanine
<220> FEATURE:
<223> OTHER INFORMATION: C-term OH

<400> SEQUENCE: 46

Ser Ala Lys Arg Arg Leu Thr Ala Gly
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Beta-homoLeu
<220> FEATURE:
<223> OTHER INFORMATION: C-term OH
```

<400> SEQUENCE: 47

Ser Ala Lys Arg Arg Leu Phe Gly
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Beta-homoLeu
<220> FEATURE:
<221> NAME/KEY: MOD_RES
<222> LOCATION: (7)..(7)
<223> OTHER INFORMATION: 3-thienyl alanine
<220> FEATURE:
<223> OTHER INFORMATION: C-term OH

<400> SEQUENCE: 48

Ser Ala Lys Arg Arg Leu Ala Gly
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: NMeArg

<400> SEQUENCE: 49

Arg Arg Leu Ile Phe
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DimethylLys

<400> SEQUENCE: 50

Arg Lys Leu Ile Phe
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term 3PBA

<400> SEQUENCE: 51

```
Ser Ala Lys Arg Arg Leu
1               5

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Leu Ile Phe
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 1-(3,5-dichlorophenyl)-5-methyl-1H-
      1,2,4-triazole-3-carbonyl

<400> SEQUENCE: 53

Arg Leu Ile Phe
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 4FPhe

<400> SEQUENCE: 54

Arg Leu Asn Phe
1

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 55

Xaa Arg Leu Ile Phe
1               5

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 56

Ala Leu Ile Phe
1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 2-furylalanine

<400> SEQUENCE: 57

Arg Leu Ile Ala
1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 2-thienyl alanine

<400> SEQUENCE: 58

Arg Leu Ile Ala
1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 3-thienyl alanine

<400> SEQUENCE: 59

Arg Leu Ile Ala
1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Cyclobutylalanine

<400> SEQUENCE: 60

Arg Leu Ile Ala
1

<210> SEQ ID NO 61
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Cyclopentylalanine

<400> SEQUENCE: 61

Arg Leu Ile Ala
1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Cyclohexylalanine

<400> SEQUENCE: 62

Arg Leu Ile Ala
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 3-pyridylalanine

<400> SEQUENCE: 63

Arg Leu Ile Ala
1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 4-pyridylalanine

<400> SEQUENCE: 64

Arg Leu Ile Ala
1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 65

Tyr Ile Thr Asp
1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Tyr Thr Asp
1
```